United States Patent [19]
Küber et al.

[11] Patent Number: 5,840,947
[45] Date of Patent: Nov. 24, 1998

[54] ORGANOMETALLIC COMPOUND

[75] Inventors: Frank Küber, Oberursel; Michael Riedel, Frankfurt; Bernd Bachmann, Eppstein; Andreas Winter, Glashütten, all of Germany

[73] Assignee: Targor GmbH, Germany

[21] Appl. No.: 648,820

[22] Filed: May 16, 1996

[30] Foreign Application Priority Data

May 16, 1995 [DE] Germany .................. 195 17 851.3

[51] Int. Cl.⁶ .................. C07F 17/00; C08F 4/42
[52] U.S. Cl. .................. 556/8; 556/11; 556/12; 556/13; 556/19; 556/20; 556/42; 556/43; 556/51; 556/52; 556/53; 556/57; 556/58; 502/155; 526/160; 526/943; 526/127
[58] Field of Search .................. 556/8, 11, 12, 556/13, 19, 20, 42, 43, 51, 52, 53, 57, 58

[56] References Cited

U.S. PATENT DOCUMENTS

| | | |
|---|---|---|
| 4,769,510 | 9/1988 | Kaminsky et al. . |
| 5,243,001 | 9/1993 | Winter et al. . |
| 5,278,264 | 1/1994 | Spaleck et al. . |
| 5,416,178 | 5/1995 | Winter et al. . |
| 5,554,776 | 9/1996 | Langhauser et al. ............ 556/11 |
| 5,585,509 | 12/1996 | Langhauser et al. ............ 556/11 |

FOREIGN PATENT DOCUMENTS

| | | |
|---|---|---|
| 2039214 | of 0000 | Canada . |
| 0 185 918 | 7/1986 | European Pat. Off. . |
| 379 758 | 1/1989 | European Pat. Off. . |
| 574 597 | 6/1992 | European Pat. Off. . |
| 545 304 | 11/1992 | European Pat. Off. . |
| 638 593 | 8/1993 | European Pat. Off. . |
| 0 576 970 A1 | 1/1994 | European Pat. Off. . |
| 608 054 | 1/1994 | European Pat. Off. . |
| 611 773 | 2/1994 | European Pat. Off. . |
| 650 973 | 10/1994 | European Pat. Off. . |
| 3726067 A1 | 2/1989 | Germany . |

OTHER PUBLICATIONS

Ewen et al., "Crystal Structures and Stereospecific Propylene Polymerizations with Chiral Hafnium Metallocene Catalysts", J. Am. Chem. Soc. (1987), 109, pp. 6544–6545.

*Primary Examiner*—David W Wu
*Attorney, Agent, or Firm*—Connolly & Hutz

[57] ABSTRACT

The present invention relates to a metallocene compound of the formula I $$R^5{}_n Cp^1 Cp^2 M^1 R^1 R^2 \qquad (I)$$

where $Cp^1$ and $Cp^2$ are, independently of one another, identical or different and are each an unsubstituted or substituted cyclopentadienyl group, n=zero or 1, $R^5$ is a bridge, $M^1$ is a metal of group IVb, Vb or VIb of the Periodic Table of the Elements, $R^1$ and $R^2$ are identical or different and are each a hydrogen atom or a $C_1$–$C_{40}$-group, wherein at least one of the two groups $Cp^1$ and $Cp^2$ is a substituted cyclopentadienyl group which bears at least one cyclic $C_3$–$C_{30}$-group containing at least one heteroatom in the ring, or which bears a fused-on $C_2$–$C_{30}$ ring system containing at least one heteroatom in the ring.

The metallocene compound can be used as a catalyst component for olefin polymerization.

13 Claims, No Drawings

ORGANOMETALLIC COMPOUND

The present invention relates to a metallocene compound containing specific cyclopentadienyl derivatives as ligands, which metallocene compound can advantageously be used as a catalyst component in the preparation of polyolefins.

Polyolefins are important for the production of films, plates or large hollow bodies or moldings, for example pipes.

The preparation of polyolefins using soluble metallocene compounds in combination with aluminoxanes or other cocatalysts which, owing to their Lewis acidity, can convert the neutral metallocene into a cation and stabilize the latter are known from the literature.

Soluble metallocene compounds based on bis (cyclopentadienyl)zirconium dialkyl or dihalide in combination with oligomeric aluminoxanes can polymerize ethylene with good activity and propylene with moderate activity. Polyethylene having a narrow molecular weight distribution and intermediate molecular weight is obtained. The polypropylene prepared in this way is atactic and has a very low molecular weight.

The preparation of isotactic polypropylene is possible by means of ethylenebis(4,5,6,7-tetrahydro-1-indenyl) zirconium dichloride together with an aluminoxane in a suspension polymerization (cf. EP 185 918). The polymer has a narrow molecular weight distribution.

Also proposed has been a specific preactivation method for the metallocene using an aluminoxane, which leads to a considerable increase in the activity of the catalyst system and to a distinct improvement in the particle morphology of the polymer (EP 0 302 424).

Furthermore, catalysts based on ethylenebisindenyl-hafnium dichloride and ethylenebis (4,5,6,7-tetrahydro-1-indenyl)hafnium dichloride and methylaluminoxane are known, and these can be used to prepare relatively high molecular weight polypropylenes by suspension polymerization (cf. J. Am. Chem. Soc. (1987), 109, 6544).

Also known are metallocenes which have aromatic π ligands fixed by a bridge and bearing substituents in the 2 position (EP 0 485 822) or in the 2 and 4 positions (EP 0 530 647).

It is therefore an object of the invention to find a novel catalyst system which is suitable for the preparation of polyolefins.

It has now surprisingly been found that this object is achieved by metallocenes containing specific cyclopentadienyl derivatives as ligands.

At least one ligand of the metallocenes of the invention is a cyclopentadienyl derivative which contains at least one heteroatom as constituent of a ring system substituted or fused onto the cyclopentadienyl group (e.g. methylcyclopentadienyl, indenyl, 2-methylindenyl or fluorenyl).

The present invention accordingly provides a metallocene compound of the formula I

$$R^5{}_n Cp^1 Cp^2 M^1 R^1 R^2 \qquad (I)$$

where $Cp^1$ and $Cp^2$ are, independently of one another, identical or different and are each an unsubstituted or substituted cyclopentadienyl group, n=zero or 1, $R^5$ is a bridge, $M^1$ is a metal of group IVb, Vb or VIb of the Periodic Table of the Elements, $R^1$ and $R^2$ are identical or different and are each a hydrogen atom or a $C_1$–$C_{40}$-group, wherein at least one of the two groups $Cp^1$ and $Cp^2$ is a substituted cyclopentadienyl group which bears at least one cyclic $C_3$–$C_{30}$-group containing at least one heteroatom in the ring, or which bears a fused-on $C_2$–$C_{30}$ ring system containing at least one heteroatom in the ring.

For the purposes of the present invention, the term heteroatom means all elements of the Periodic Table of the Elements with the exception of carbon (C) and hydrogen (H). Preferred heteroatoms are oxygen (O), nitrogen (N), phosphorus (P), silicon (Si) and sulfur (S) which can bear radicals which are not constituents of the ring, e.g. oxygen (if the heteroatom is not oxygen) or hydrocarbon-containing $C_1$–$C_{40}$-radicals such as $C_1$–$C_{10}$-alkyl or $C_6$–$C_{14}$-aryl.

In the metallocene compound of the invention having the formula I, $M^1$ is a metal of group IVb, Vb or VIb of the Periodic Table of the Elements, for example titanium, zirconium, hafnium, vanadium, niobium, tantalum, chromium, molybdenum or tungsten, preferably a metal of group IVb such as zirconium, hafnium or titanium.

The radicals $R^1$ and $R^2$ are identical or different and are each a hydrogen atom, a $C_1$–$C_{40}$-group such as a $C_1$–$C_{10}$-, preferably $C_1$–$C_3$-alkyl group, a $C_1$–$C_{10}$-, preferably $C_1$–$C_3$-alkoxy group, a $C_6$–$C_{14}$-, preferably $C_6$–$C_{10}$-aryl group, a $C_6$–$C_{10}$-, preferably $C_6$–$C_8$-aryloxy group, a $C_2$–$C_{10}$-, preferably $C_2$–$C_4$-alkenyl group, a $C_7$–$C_{40}$-, preferably $C_7$–$C_{10}$-arylalkyl group, a $C_7$–$C_{40}$-, preferably $C_7$–$C_{11}$-alkylaryl group, a $C_8$–$C_{40}$-, preferably $C_8$–$C_{12}$-arylalkenyl group, an OH group, a halogen atom, preferably chlorine, or an $NR^6{}_2$ group, where $R^6$ are identical or different and are each a $C_1$–$C_{10}$-alkyl, preferably $C_1$–$C_4$-alkyl group or a $C_6$–$C_{14}$-, preferably $C_6$-aryl group.

When n=zero, the compound in question is an unbridged metallocene which has no bridge $R^5$. When n=1, the metallocene is bridged.

$R^5$ is a bridge, preferably

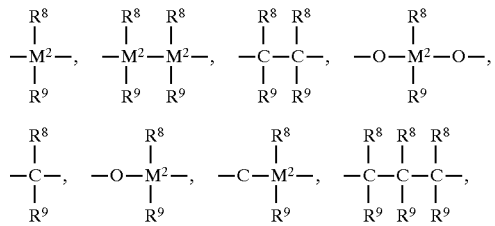

$=BR^8$, $=AlR^8$, —Ge—, —O—, —S—, $=SO$, $=SO_2$, $=NR^8$, $=CO$, $=PR^8$ or $=P(O)R^8$, where each $R^8$ and each $R^9$ is identical or different independently of the other $R^8$ and $R^9$ and is a hydrogen atom, a halogen atom, a $C_1$–$C_{10}$-, preferably $C_1$–$C_4$-alkyl group, in particular a methyl group, a $C_1$–$C_{10}$-fluoroalkyl, preferably $CF_3$ group, a $C_6$–$C_{14}$-, preferably $C_6$–$C_{10}$-aryl group, a $C_6$–$C_{10}$-fluoroalkyl, preferably pentafluorophenyl group, a $C_1$–$C_{10}$-, preferably $C_1$–$C_4$-alkoxy group, in particular a methoxy group, a $C_2$–$C_{10}$-, preferably $C_2$–$C_4$-alkenyl group, a $C_7$–$C_{40}$-, preferably $C_7$–$C_{10}$-arylalkyl group, a $C_8$–$C_{40}$-, preferably $C_8$–$C_{12}$-arylalkenyl group or a $C_7$–$C_{40}$-, preferably $C_7$–$C_{12}$-alkylaryl group, or $R^8$ and $R^9$ in each case together with the atoms connecting them form one or more rings. $M^2$ is silicon, germanium or tin, preferably silicon or germanium.

Examples of substituted cyclopentadienyl groups are: methylcyclopentadienyl, methyl-tert-butylcyclopentadienyl, tert-butylcyclopentadienyl, isopropylcyclopentadienyl, dimethylcyclopentadienyl, dimethylcyclopentadienyl, trimethylethylcyclopentadienyl, 5-phenylcyclopentadienyl, diphenylcyclopentadienyl, indenyl, 2-methylindenyl, 2-ethylindenyl, 3-methylindenyl, 3-tert-butylindenyl, 3-trimethylsilylindenyl, 2-methyl-4-phenylindenyl, 2-ethyl-4-phenylindenyl, 2-methyl-4-naphthylindenyl, 2-methyl-4- isopropylindenyl, benzoindenyl, 2-methyl-4,5-benzoindenyl, 2-methyl-α-acenaphthindenyl, 2-methyl-4,6-diisopropylindenyl, fluorenyl, 4-methylfluorenyl or 2,7-di-tert-butylfluorenyl.

At least one of the substituted or unsubstituted cyclopentadienyl groups bears at least one cyclic $C_3$–$C_{30}$-, preferably $C_4$–$C_{20}$-, in particular $C_5$–$C_{10}$-radical containing at least one heteroatom in the ring, or bears a fused-on $C_2$–$C_{30}$, preferably $C_3$–$C_{20}$, in particular $C_4$–$C_{10}$ ring system containing at least one heteroatom in the ring. In determining the number of carbon atoms in the fused-on heteroatom-containing $C_2$–$C_{30}$ ring system, the ring carbons of the cyclopentadienyl group are not counted. Thus, for example, the fused-on heteroatom-containing ring of 4,5-(2-azobenzo)indenyl has three ring carbons. The cyclic $C_3$–$C_{30}$-radical and the fused-on $C_2$–$C_{30}$ ring system can be saturated or unsaturated, (e.g. aromatic) and, as heteroatoms in the ring, preferably contain O, N, P, Si or S which can also bear radicals which are not constituents of the ring. Examples of such radicals are oxygen (if the heteroatom is not oxygen) or radicals $R^{14}$ which are $C_1$–$C^{40}$-groups such as a $C_1$–$C_{10}$-, preferably $C_1$–$C_3$-alkyl group, a $C_1$–$C_{10}$-, preferably $C_1$–$C_3$-alkoxy group, a $C_6$–$C_{14}$-, preferably $C_6$–$C_{10}$-aryl group, a $C_6$–$C_{10}$-, preferably $C_6$–$C_8$-aryloxy group, a $C_2$–$C_{10}$-, preferably $C_2$–$C_4$-alkenyl group, a $C_7$–$C_{40}$-, preferably $C_7$–$C_{10}$-arylalkyl group, a $C_7$–$C_{40}$-, preferably $C_7$–$C_{11}$-alkylaryl group, a $C_8$–$C_{40}$-, preferably $C_8$–$C_{12}$-arylalkenyl group, a halogen atom, preferably chlorine, or an $NR^6_2$ group, where $R^6$ is a $C_1$–$C_{10}$-, preferably $C_1$–$C_4$-alkyl group or a $C_6$–$C_{14}$-, preferably $C_6$-aryl group. Examples of substituted ring heteroatoms are

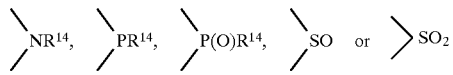

Preferred metallocene compounds of the formula (I) have the formula II

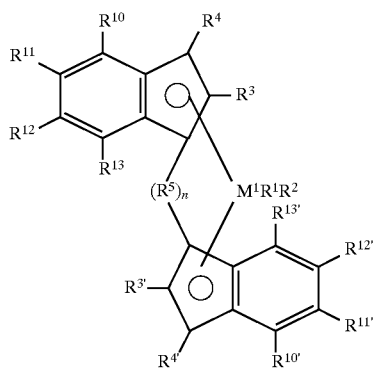

where $M^1$ is a metal of group IVb, Vb or VIb of the Periodic Table of the Elements, $R^1$ and $R^2$ are identical or different and are each a hydrogen atom or a $C_1$–$C_{40}$-group, the radicals $R^3$ and $R^{3'}$ are identical or different and are each a hydrogen atom, a halogen atom, a $C_1$–$C_{10}$-alkyl group which can be halogenated, a $C_6$–$C_{14}$-aryl group which can be halogenated, an $NR^7_2$—, —$SR^7$—, —$OSiR^7_3$—, —$SiR^7_3$— or —$PR^7_2$ radical, where $R^7$ is a halogen atom, a $C_1$–$C_{10}$-alkyl group or a $C_6$–$C_{14}$-aryl group, $R^4$ and $R^{4'}$ are identical or different and are each a hydrogen atom, a halogen atom, a $C_1$–$C_{10}$-alkyl group which can be halogenated, a $C_6$–$C_{14}$-aryl group which can be halogenated, an $NR^7_2$—, —$SR^7$—, —$OSiR^7_3$—, —$SiR^7_3$— or —$PR^7_2$ radical, where $R^7$ is a halogen atom, a $C_1$–$C_{10}$-alkyl group or a $C_6$–$C_{14}$-aryl group, n=zero or 1, $R^5$ is a bridge, preferably

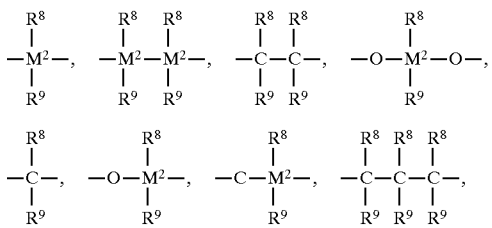

$=BR^8$, $=AlR^8$, —Ge—, —O—, —S—, $=SO$, $=SO_2$, $=NR^8$, $=CO$, $=PR^8$ or $=P(O)R^8$, where each $R^8$ and each $R^9$ is, independently of other $R^8$ and $R^9$, identical or different and is a hydrogen atom, a halogen atom or a $C_1$–$C_{40}$-group such as a $C_1$–$C_{10}$-alkyl group, a $C_1$–$C_{10}$-fluoroalkyl group, a $C_1$–$C_{10}$-alkoxy group, a $C_6$–$C_{14}$-aryl group, a $C_6$–$C_{10}$-fluoroalkyl group, a $C_6$–$C_{10}$-aryloxy group, a $C_2$–$C_{10}$-alkenyl group, a $C_7$–$C_{40}$-arylalkyl group, a $C_7$–$C_{40}$-alkylaryl group or a $C_8$–$C_{40}$-arylalkenyl group, or $R^8$ and $R^9$, in each case together with the atoms connecting them, form one or more rings, $M^2$ is silicon, germanium or tin and $R^{10}$, $R^{11}$, $R^{12}$, $R^{13}$, $R^{10'}$, $R^{11'}$, $R^{12'}$ and $R^{13'}$ are identical or different and are each a hydrogen atom or a $C_1$–$C_{40}$-radical such as a $C_1$–$C_{10}$-alkyl group, a $C_1$–$C_{10}$-fluoroalkyl group, a $C_1$–$C_{10}$-alkoxy group, a $C_6$–$C_{30}$-aryl group, a $C_6$–$C_{10}$-fluoroaryl group, a $C_6$–$C_{10}$-aryloxy group, a $C_2$–$C_{10}$-alkenyl group, a $C_7$–$C_{40}$-arylalkyl group, a $C_7$–$C_{40}$-alkylaryl group or a $C_8$–$C_{40}$-arylalkenyl group, or two or more of the radicals $R^{10}$, $R^{11}$, $R^{12}$, $R^{13}$, $R^{10'}$, $R^{11'}$, $R^{12'}$ and $R^{13'}$ together form a fused-on $C_6$–$C_{30}$ ring system, where at least one of the radicals $R^{10}$, $R^{11}$, $R^{12}$, $R^{13}$, $R^{10'}$, $R^{11'}$, $R^{12'}$ and $R^{13'}$ is a cyclic $C_3$–$C_{30}$-radical containing at least one heteroatom in the ring, or two or more of the radicals $R^{10}$, $R^{11}$, $R^{12}$, $R^{13}$, $R^{10'}$, $R^{11'}$, $R^{12'}$ and $R^{13'}$ together form a fused-on $C_2$–$C_{30}$ ring system containing at least one heteroatom in the ring.

For the purposes of the present invention, the term heteroatom means all elements of the Periodic Table of the Elements with the exception of carbon (C) and hydrogen (H). Preferred heteroatoms are oxygen (O), nitrogen (N), phosphorus (P), silicon (Si) and sulfur (S) which can bear radicals which are not constituents of the ring, e.g. oxygen (if the heteroatom is not oxygen) or hydrocarbon-containing $C_1$–$C_{40}$-radicals such as $C_1$–$C_{10}$-alkyl or $C_6$–$C_{14}$-aryl.

In the metallocene compound of the invention having the formula II, $M^1$ is a metal of group IVb, Vb or VIb of the Periodic Table of the Elements, for example titanium, zirconium, hafnium, vanadium, niobium, tantalum, chromium, molybdenum or tungsten, preferably a metal of group IVb such as zirconium, hafnium or titanium.

The radicals $R^1$ and $R^2$ are identical or different and are each a hydrogen atom, a $C_1$–$C_{40}$-group such as a $C_1$–$C_{10}$-, preferably $C_1$–$C_3$-alkyl group, a $C_1$–$C_{10}$-, preferably $C_1$–$C_3$-alkoxy group, a $C_6$–$C_{14}$, preferably $C_6$–$C_{10}$-aryl group, a $C_6$–$C_{10}$-, preferably $C_6$–$C_8$-aryloxy group, a $C_2$–$C_{10}$-, preferably $C_2$–$C_4$-alkenyl group, a $C_7$–$C_{40}$-, preferably $C_7$–$C_{10}$- arylalkyl group, a $C_7$–$C_{40}$-, preferably $C_7$–$C_{11}$-alkylaryl group, a $C_8$–$C_{40}$-, preferably $C_8$–$C_{12}$-arylalkenyl group, an OH group, a halogen atom, preferably chlorine, or an $NR^6{}_2$ group, where $R^6$ are identical or different and are each a $C_1$–$C_{10}$-alkyl, preferably $C_1$–$C_4$-alkyl group or a $C_6$–$C_{14}$-, preferably $C_6$-aryl group.

The radicals $R^3$ and $R^{3'}$ are identical or different and are each a hydrogen atom, a halogen atom, preferably fluorine, chlorine or bromine, a $C_1$–$C_{10}$-, preferably $C_1$–$C_4$-alkyl group which can be halogenated, a $C_6$–$C_{14}$-, preferably $C_6$–$C_{10}$-aryl group which can be halogenated, an —$NR^7{}_2$—, —$SR^7$—, —$OSiR^7{}_3$—, —$SiR^7{}_3$— or —$PR^7{}_2$ radical, where $R^7$ is a halogen atom, preferably chlorine, or a $C_1$–$C_{10}$-, preferably $C_1$–$C_4$-alkyl group or a $C_6$–$C_{14}$-, preferably $C_6$–$C_{10}$-aryl group.

The radicals $R^4$ and $R^{4'}$ are identical or different and are each a hydrogen atom, a halogen atom, preferably fluorine, chlorine or bromine, a $C_1$–$C_{10}$-, preferably $C_1$–$C_4$-alkyl group which can be halogenated, a $C_6$–$C_{14}$-, preferably $C_6$–$C_{10}$-aryl group, an —$NR^7{}_2$—, —$SR^7$—, —$OSiR^7{}_3$—, —$SiR^7{}_3$— or —$PR^7{}_2$ radical, where $R^7$ is a halogen atom, preferaby chlorine, or a $C_1$–$C_{10}$-, preferably $C_1$–$C_4$-alkyl group or a $C_6$–$C_{14}$-, preferably $C_6$–$C_{10}$-aryl group.

When n=zero, the compound in question is an unbridged metallocene which has no bridge $R^5$. When n=1, the metallocene is bridged.

$R^5$ is a bridge, preferably

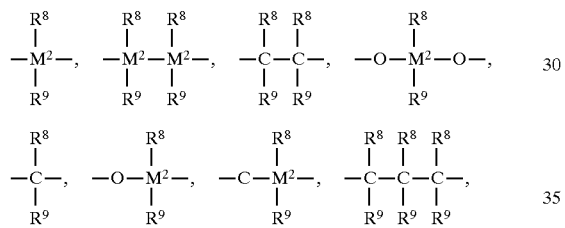

=$BR^8$, =$AlR^8$, —Ge—, —O—, —S—, =SO, =$SO_2$, =$NR^8$, =CO, =$PR^8$ or =$P(O)R^8$, where each $R^8$ and each $R^9$ is, independently of other $R^8$ and $R^9$, identical or different and is a hydrogen atom, a halogen atom a $C_1$–$C_{10}$-, preferably $C_1$–$C_4$-alkyl group, in particular a methyl group, a $C_1$–$C_{10}$-fluoroalkyl, preferably $CF_3$- group, a $C_6$–$C_{14}$-, preferably $C_6$–$C_{10}$-aryl group, a $C_6$–$C_{10}$-fluoraryl-, preferably pentafluorophenyl group, a $C_1$–$C_{10}$-, preferably $C_1$–$C_4$-alkoxy group, in particular a methoxy group, a $C_2$–$C_{10}$-, preferably $C_2$–$C_4$-alkenyl group, a $C_7$–$C_{40}$-, preferably $C_7$–$C_{10}$-arylalkyl group, a $C_8$–$C_{40}$-, preferably $C_8$–$C_{12}$-arylalkenyl group or a $C_7$–$C_{40}$-, preferably $C_7$–$C_{12}$-alkylaryl group, or $R^8$ and $R^9$ in each case together with the atoms connecting them form one or more rings, $M^2$ is silicon, germanium or tin, preferably silicon or germanium.

At least one of the radicals $R^{10}$, $R^1$, $R^{12}$, $R^{13}$, $R^{10'}$, $R^{11'}$, $R^{12'}$, $R^{13'}$ is a cyclic $C_3$–$C_{30}$-, preferably $C_4$–$C_{20}$-, in particular $C_5$–$C_{10}$-radical containing at least one heteroatom in the ring, or two or more of the radicals $R^{10}$, $R^{11}$, $R^{12}$, $R^{13}$, $R^{10'}$, $R^{11'}$, $R^{12'}$, $R^{13'}$ together form a fused-on $C_2$–$C_{30}$-, preferaby $C_3$–$C_{20}$-, in particular $C_r$–$C_{10}$ ring system containing at least one heteroatom in the ring. In determining the number of carbon atoms of the fused-on heteroatom-containing $C_2$–$C_{30}$ ring system, the ring carbons of the cyclopentadienyl group are not counted. Thus, for example, the fused-on heteroatom-containing ring of 4,5-(2-azobenzo)indenyl has three ring carbons. The cyclic $C_3$–$C_{30}$-radical and the fused-on $C_2$–$C_{30}$ ring system can be saturated or unsaturated, (e.g. aromatic) and, as heteroatoms in the ring, preferably contain O, N, P or S which can also bear radicals which are not constituents of the ring. Examples of such radicals are oxygen (if the heteroatom is not oxygen) or radicals $R^{14}$ which are each a $C_1$–$C_{40}$-group such as a $C_1$–$C_{10}$-, preferably $C_1$–$C_3$-alkyl group, a $C_1$–$C_{10}$-, preferably $C_1$–$C_3$-alkoxy group, a $C_6$–$C_{14}$-, preferably $C_6$–$C_{10}$-aryl group, a $C_6$–$C_{10}$-, preferably $C_6$–$C_8$-aryloxy group, a $C_2$–$C_{10}$-, preferably $C_2$–$C_4$-alkenyl group, a $C_7$–$C_{40}$-, preferably $C_7$–$C_{10}$-arylalkyl group, a $C_7$–$C_{40}$-, preferably $C_7$–$C_{11}$-alkylaryl group, a $C_8$–$C_{40}$-, preferably $C_8$–$C_{12}$-arylalkenyl group, a halogen atom, preferably chlorine, or an $NR^6{}_2$ group, where $R^6$ is a $C_1$–$C_{10}$-, preferably $C_1$–$C_4$-alkyl group or a $C_6$–$C_{14}$-, preferably $C_6$-aryl group. Examples of substituted ring heteroatoms are

For compounds of the formula II, it is preferred that $M^1$ is zirconium or hafnium, the radicals $R^1$ and $R^2$ are identical or different, preferably identical, and are each a $C_1$–$C_4$-alkyl group, an $NR^6{}_2$ group, where $R^6$ is a $C_1$–$C_4$-alkyl radical or a halogen atom, the radicals $R^3$ and $R^{3'}$ are identical or different, preferably identical, and are each a $C_1$–$C_4$-alkyl group such as methyl, ethyl or isobutyl or a $C_6$–$C_{10}$-aryl group such as phenyl, the radicals $R^4$ and $R^{4'}$ are identical and are each a hydrogen atom, $R^5$

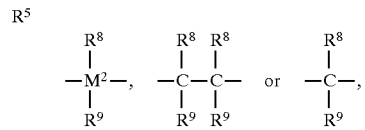

where $M^2$ is silicon or germanium and $R^8$ and $R^9$ are identical or different, preferably identical, and are each a $C_1$–$C_4$-alkyl group such as methyl, ethyl or isobutyl or a $C_6$–$C_{10}$-aryl group such as phenyl, $R^{10}$ and $R^{10'}$ are identical or different, preferably identical, and are each a saturated or unsaturated cyclic $C_3$–$C_{30}$-, preferably $C_4$–$C_{20}$-radical containing in the ring at least one heteroatom such as O, N or S which can bear radicals $R^{14}$ such as a $C_1$–$C_4$-alkyl group, $R^{11}$, $R^{12}$, $R^{11'}$, $R^{12'}$ are identical or different, preferably $R^{11}$ is identical to $R^{11'}$ and $R^{12}$ is identical to $R^{12'}$, and are each a hydrogen atom, a $C_1$–$C_{10}$-radical such as $C_1$–$C_4$-alkyl or $C_6$–$C_{10}$-aryl, or a saturated or unsaturated cyclic $C_3$–$C_{20}$-radical having in the ring at least one heteroatom such as O, N or S which can bear radicals $R^{14}$ such as a $C_1$–$C_4$-alkyl group, or at least two of the radicals $R^{10}$, $R^{11}$ and $R^{12}$ or $R^{10'}$, $R^{11'}$ and $R^{12'}$ together form a fused-on $C_2$–$C_{20}$ ring system containing at least one heteroatom in the ring, and $R^{13}$ is identical to $R^{13'}$ and is a hydrogen atom.

Particular preference is given to compounds of the formula I in which $M^1$ is zirconium, $R^1$ and $R^2$ are identical and are chlorine, the radicals $R^3$ and $R^{3'}$ are identical and are each a $C_1$–$C_4$-alkyl group or a $C_6$–$C_{10}$-aryl group, $R^4$ and $R^{4'}$ are hydrogen, $R^5$ is

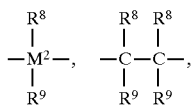

where $M^2$ is silicon, and $R^8$ and $R^9$ are identical or different and are each a $C_1$–$C_4$-alkyl group or a $C_6$–$C_{10}$-aryl group, the radicals $R^{10}$ and $R^{10'}$ are identical and are each a saturated or unsaturated cyclic $C_4$–$C_9$-radical containing at least one heteroatom such as S, N, P or O in the ring.

Examples of particularly preferred radicals $R^3$ and $R^{3'}$ are: methyl, ethyl, isopropyl, isobutyl, butyl and phenyl.

Examples of particularly preferred cyclic $C_3$–$C_{30}$-radicals are 1-furanyl, 1-furfuryl, 2-N-methylindolyl, 4-pyridyl, 2-pyridyl, 8-quinolyl, 3-quinolyl, 5-pyrimidyl.

Examples of compounds of the formula I are:
dimethylsilanediylbis(2-methyl-4-(2-pyridyl)indenyl)zirconium dichloride,
dimethylsilanediylbis(2-ethyl-4-(2-pyridyl)indenyl)zirconium dichloride,
dimethylsilanediylbis(2-n-butyl-4-(2-pyridyl)indenyl)zirconium dichloride,
dimethylsilanediylbis(2-i-propyl-4-(2-pyridyl)indenyl)zirconium dichloride,
dimethylsilanediylbis(2-phenyl-4-(2-pyridyl)indenyl)zirconium dichloride,
dimethylsilanediylbis(2-trimethylsilyl-4-(2-pyridyl)indenyl)zirconium dichloride,
methylphenylsilanediylbis(2-methyl-4-(2-pyridyl)indenyl)zirconium dichloride,
diphenylsilanediylbis(2-methyl-4-(2-pyridyl)indenyl)zirconium dichloride,
1,2-ethanediylbis(2-methyl-4-(2-pyridyl)indenyl)zirconium dichloride,
dimethylsilanediylbis(2-methyl-4-(2-pyridyl)-7-methylindenyl)zirconium dichloride,
dimethylsilanediylbis(2-ethyl-4-(2-pyridyl)-7-methylindenyl)zirconium dichloride,
dimethylsilanediylbis(2-n-butyl-4-(2-pyridyl)-7-methylindenyl)zirconium dichloride,
dimethylsilanediylbis(2-i-propyl-4-(2-pyridyl)-7-methylindenyl)zirconium dichloride,
dimethylsilanediylbis(2-phenyl-4-(2-pyridyl)-7-methylindenyl)zirconium dichloride,
dimethylsilanediylbis(2-trimethylsilyl-4-(2-pyridyl)-7-methylindenyl)zirconium dichloride,
methylphenylsilanediylbis(2-methyl-4-(2-pyridyl)-7-methylindenyl)zirconium dichloride,
diphenylsilanediylbis(2-methyl-4-(2-pyridyl)-7-methylindenyl)zirconium dichloride,
1,2-ethanediylbis(2-methyl-4-(2-pyridyl)-7-methylindenyl)zirconium dichloride,
dimethylsilanediylbis(2-methyl-4-(2-pyridyl)-6-i-propylindenyl)zirconium dichloride,
dimethylsilanediylbis(2-ethyl-4-(2-pyridyl)-6-i-propylindenyl)zirconium dichloride,
dimethylsilanediylbis(2-n-butyl-4-(2-pyridyl)-6-i-propylindenyl)zirconium dichloride,
dimethylsilanediylbis(2-i-propyl-4-(2-pyridyl)-6-i-propylindenyl)zirconium dichloride,
dimethylsilanediylbis(2-phenyl-4-(2-pyridyl)-6-i-propylindenyl)zirconium dichloride,
dimethylsilanediylbis(2-trimethylsilyl-4-(2-pyridyl)-6-i-propylindenyl)zirconium dichloride,
methylphenylsilanediylbis(2-methyl-4-(2-pyridyl)-6-i-propylindenyl)zirconium dichloride,
diphenylsilanediylbis(2-methyl-4-(2-pyridyl)-6-i-propylindenyl)zirconium dichloride,
1,2-ethanediylbis(2-methyl-4-(2-pyridyl)-6-i-propylindenyl)zirconium dichloride,
dimethylsilanediylbis(2-methyl-4,6-bis(2-pyridyl)indenyl)zirconium dichloride,
dimethylsilanediylbis(2-ethyl-4,6-bis(2-pyridyl)indenyl)zirconium dichloride,
dimethylsilanediylbis(2-n-butyl-4,6-bis(2-pyridyl)indenyl)zirconium dichloride,
dimethylsilanediylbis(2-i-propyl-4,6-bis(2-pyridyl)indenyl)zirconium dichloride,
dimethylsilanediylbis(2-phenyl-4,6-bis(2-pyridyl)indenyl)zirconium dichloride,
dimethylsilanediylbis(2-trimethylsilyl-4,6-bis-(2-pyridyl)indenyl)zirconium dichloride,
methylphenylsilanediylbis(2-methyl-4,6-bis(2-pyridyl)indenyl)zirconium dichloride,
diphenylsilanediylbis(2-methyl-4,6-bis(2-pyridyl)indenyl)zirconium, dichloride,
1,2-ethanediylbis(2-methyl-4,6-bis(2-pyridyl)indenyl)zirconium dichloride,
dimethylsilanediylbis(2-methyl-4-(3-quinolyl)indenyl)zirconium dichloride,
dimethylsilanediylbis(2-ethyl-4-(3-quinolyl)indenyl)zirconium dichloride,
dimethylsilanediylbis(2-n-butyl-4-(3-quinolyl)indenyl)zirconium dichloride,
dimethylsilanediylbis(2-i-propyl-4-(3-quinolyl)indenyl)zirconium dichloride,
dimethylsilanediylbis(2-phenyl-4-(3-quinolyl)indenyl)zirconium dichloride,
dimethylsilanediylbis(2-trimethylsilyl-4-(3-quinolyl)indenyl)zirconium dichloride,
methylphenylsilanediylbis(2-methyl-4-(3-quinolyl)indenyl)zirconium dichloride,
diphenylsilanediylbis(2-methyl-4-(3-quinolyl)indenyl)zirconium dichloride,
1,2-ethanediylbis(2-methyl-4-(3-quinolyl)indenyl)zirconium dichloride,
dimethylsilanediylbis(2-methyl-4-(8-quinolyl)indenyl)zirconium dichloride,
dimethylsilanediylbis(2-ethyl-4-(8-quinolyl)indenyl)zirconium dichloride,
dimethylsilanediylbis(2-n-butyl-4-(8-quinolyl)indenyl)zirconium dichloride,
dimethylsilanediylbis(2-i-propyl-4-(8-quinolyl)indenyl)zirconium dichloride,
dimethylsilanediylbis(2-phenyl-4-(8-quinolyl)indenyl)zirconium dichloride,
dimethylsilanediylbis(2-trimethylsilyl-4-(8-quinolyl)indenyl)zirconium dichloride,
methylphenylsilanediylbis(2-methyl-4-(8-quinolyl)indenyl)zirconium dichloride,
diphenylsilanediylbis(2-methyl-4-(8-quinolyl)indenyl)zirconium dichloride,
1,2-ethanediylbis(2-methyl-4-(8-quinolyl)indenyl)zirconium dichloride,
dimethylsilanediylbis(2-methyl-4,5-(2-azabenzo)indenyl)zirconium dichloride,
dimethylsilanediylbis(2-ethyl-4,5-(2-azabenzo)indenyl)zirconium dichloride,
dimethylsilanediylbis(2-n-butyl-4,5-(2-azabenzo)indenyl)zirconium dichloride,
dimethylsilanediylbis(2-i-propyl-4,5-(2-azabenzo)indenyl)zirconium dichloride, dimethylsilanediylbis(2-phenyl-4,5-(2-azabenzo)indenyl) zirconium dichloride,
dimethylsilanediylbis(2-trimethylsilyl-4,5-(2-azabenzo)indenyl)zirconium dichloride,
methylphenylsilanediylbis(2-methyl-4,5-(2-azabenzo)indenyl)zirconium dichloride,
diphenylsilanediylbis(2-methyl-4,5-(2-azabenzo)indenyl) zirconium dichloride,
1,2-ethanediylbis(2-methyl-4,5-(2-azabenzo)indenyl) zirconium dichloride,
dimethylsilanediylbis(2-methyl-4-(4-pyridyl)indenyl) zirconium dichloride,
dimethylsilanediylbis(2-ethyl-4,5-(4-pyridyl)indenyl) zirconium dichloride,
dimethylsilanediylbis(2-n-butyl-4,5-(4-pyridyl)indenyl) zirconium dichloride,
dimethylsilanediylbis(2-i-propyl-4,5-(4-pyridyl)indenyl) zirconium dichloride,
dimethylsilanediylbis(2-phenyl-4,5-(4-pyridyl)indenyl) zirconium dichloride,
dimethylsilanediylbis(2-trimethylsilyl-4,5-(4-pyridyl) indenyl)zirconium dichloride,
methylphenylsilanediylbis(2-methyl-4,5-(4-pyridyl) indenyl)zirconium dichloride,
diphenylsilanediylbis(2-methyl-4,5-(4-pyridyl)indenyl) zirconium dichloride,
1,2-ethanediylbis(2-methyl-4,5-(4-pyridyl)indenyl) zirconium dichloride,
dimethylsilanediylbis(2-methyl-4-(5-pyrimidyl)indenyl) zirconium dichloride,
dimethylsilanediylbis(2-ethyl-4,5-(5-pyrimidyl)indenyl) zirconium dichloride,
dimethylsilanediylbis(2-n-butyl-4,5-(5-pyrimidyl)indenyl) zirconium dichloride,
dimethylsilanediylbis(2-i-propyl-4,5-(5-pyrimidyl)indenyl) zirconium dichloride,
dimethylsilanediylbis(2-phenyl-4,5-(5-pyrimidyl)indenyl) zirconium dichloride,
dimethylsilanediylbis(2-trimethylsilyl-4,5-(5-pyrimidyl) indenyl)zirconium dichloride,
methylphenylsilanediylbis(2-methyl-4,5-(5-pyrimidyl) indenyl)zirconium dichloride,
diphenylsilanediylbis(2-methyl-4,5-(5-pyrimidyl)indenyl) zirconium dichloride,
1,2-ethanediylbis(2-methyl-4,5-(5-pyrimidyl)indenyl) zirconium dichloride,
dimethylsilanediylbis(2-methyl-4-(2-furanyl)indenyl) zirconium dichloride,
dimethylsilanediylbis(2-ethyl-4,5-(2-furanyl)indenyl) zirconium dichloride,
dimethylsilanediylbis(2-n-butyl-4,5-(2-furanyl)indenyl) zirconium dichloride,
dimethylsilanediylbis(2-i-propyl-4,5-(2-furanyl)indenyl) zirconium dichloride,
dimethylsilanediylbis(2-phenyl-4,5-(2-furanyl)indenyl) zirconium dichloride,
dimethylsilanediylbis(2-trimethylsilyl-4,5-(2-furanyl) indenyl)zirconium dichloride,
methylphenylsilanediylbis(2-methyl-4,5-(2-furanyl) indenyl)zirconium dichloride,
diphenylsilanediylbis(2-methyl-4,5-(2-furanyl)indenyl) zirconium dichloride
1,2-ethanediylbis(2-methyl-4,5-(2-furanyl)indenyl) zirconium dichloride,
dimethylsilanediylbis(2-methyl-4,5-(2-fufuryl)indenyl) zirconium dichloride,
dimethylsilanediyl(2-methyl-4,5-(2-fufuryl)indenyl)-(2-methyl-4-(2-pyridyl)indenyl)zirconium dichloride,
dimethylsilanediylbis(2-n-butyl-4,5-(2-fufuryl)indenyl) zirconium dichloride,
dimethylsilanediylbis(2-i-propyl-4,5-(2-fufuryl)indenyl) zirconium dichloride,
dimethylsilanediylbis(2-phenyl-4,5-(2-fufuryl)indenyl) zirconium dichloride,
dimethylsilanediylbis(2-trimethylsilyl-4,5-(2-fufuryl) indenyl)zirconium dichloride,
methylphenylsilanediylbis(2-methyl-4,5-(2-fufuryl) indenyl) zirconium dichloride,
diphenylsilanediylbis(2-methyl-4,5-(2-fufuryl)indenyl) zirconium dichloride,
1,2-ethanediyl(2-methyl-4,5-(2-fufuryl)indenyl)(2-methyl-4-(2-furanyl)indenyl)zirconium dichloride,
bis(2-methyl-4-(2-pyridyl)indenyl)zirconium dichloride,
dimethylsilanediylbis(4-(2-pyridyl)indenyl)zirconium dichloride,
(2-i-propyl-4-(2-pyridyl)indenyl)zirconium dichloride,
(2-phenyl-4-(2-pyridyl)indenyl)zirconium dichloride,
(2-trimethylsilyl-4-(2-pyridyl)indenyl)zirconium dichloride,
methylphenylsilanediylbis(4-(2-pyridyl)indenyl)zirconium dichloride,
diphenylsilanediylbis(4-(2-pyridyl)indenyl)zirconium dichloride,
1,2-ethanediylbis(4-(2-pyridyl)indenyl)zirconium dichloride,
bis(2-methyl-4-(2-pyridyl)-7-methylindenyl)zirconium dichloride,
dimethylsilanediylbis(4-(2-pyridyl)-7-methylindenyl) zirconium dichloride,
(2-i-propyl-4-(2-pyridyl)-7-methylindenyl)zirconium dichloride,
(2-phenyl-4-(2-pyridyl)-7-methylindenyl)zirconium dichloride,
(2-trimethylsilyl-4-(2-pyridyl)-7-methylindenyl)zirconium dichloride,
methylphenylsilanediylbis(4-(2-pyridyl)-7-methylindenyl) zirconium dichloride,
diphenylsilanediylbis(4-(2-pyridyl)-7-methylindenyl) zirconium dichloride,
1,2-ethanediylbis(4-(2-pyridyl)-7-methylindenyl)zirconium dichloride,
dimethylsilanediylbis(2-methyl-4-(2-pyridyl)-6-i-propylindenyl)hafnium dichloride,
dimethylsilanediylbis(4-(2-pyridyl)-6-i-propylindenyl) hafnium dichloride,
dimethylsilanediylbis(2-n-butyl-4-(2-pyridyl)-6-i-propylindenyl)hafnium dichloride,
bis(2-i-propyl-4-(2-pyridyl)-6-i-propylindenyl)hafnium dichloride,
dimethylsilanediylbis(2-phenyl-4-(2-pyridyl)-6-i-propylindenyl)hafnium dichloride,
dimethylsilanediylbis(2-trimethylsilyl-4-(2-pyridyl)-6-i-propylindenyl)hafnium dichloride,
methylphenylsilanediylbis(2-methyl-4-(2-pyridyl)-6-i-propylindenyl)hafnium dichloride,
diphenylsilanediylbis(2-methyl-4-(2-pyridyl)-6-i-propylindenyl)hafnium dichloride,
1,2-ethanediylbis(2-methyl-4-(2-pyridyl)-6-i-propylindenyl)hafnium dichloride,
dimethylsilanediyl(indenyl)(2-methyl-4-(3-quinolyl) indenyl)zirconium dichloride,
dimethylsilanediyl(indenyl)(2-ethyl-4-(3-quinolyl)indenyl) zirconium dichloride,
dimethylsilanediyl(indenyl)(2-n-butyl-4-(3-quinolyl) indenyl)zirconium dichloride,
dimethylsilanediyl(indenyl)(2-i-propyl-4-(3-quinolyl) indenyl)zirconium dichloride, dimethylsilanediyl(indenyl)(2-phenyl-4-(3-quinolyl) indenyl)zirconium dichloride,
dimethylsilanediyl(indenyl)(2-trimethylsilyl-4-(3-quinolyl) indenyl)zirconium dichloride,
methylphenylsilanediyl(indenyl)(2-methyl-4-(3-quinolyl) indenyl)zirconium dichloride,
diphenylsilanediyl(indenyl)(2-methyl-4-(3-quinolyl) indenyl)zirconium dichloride,
1,2-ethanediyl(indenyl)(2-methyl-4-(3-quinolyl)indenyl) zirconium dichloride,
dimethylsilanediyl(2-methylindenyl)(2-methyl-4-(8-quinolyl)indenyl)zirconium dichloride,
dimethylsilanediyl(2-methylindenyl)(2-ethyl-4-(8-quinolyl)indenyl)zirconium dichloride,
dimethylsilanediyl(2-methylindenyl)(2-n-butyl-4-(8-quinolyl)indenyl)zirconium dichloride,
dimethylsilanediyl(2-methylindenyl)(2-i-propyl-4-(8-quinolyl)indenyl)zirconium dichloride,
dimethylsilanediyl(2-methylindenyl)(2-phenyl-4-(8-quinolyl)indenyl)zirconium dichloride,
dimethylsilanediyl(2-methylindenyl)(2-trimethylsilyl-4-(8-quinolyl)indenyl)zirconium dichloride,
methylphenylsilanediyl(2-methylindenyl)(2-methyl-4-(8-quinolyl)indenyl)zirconium dichloride,
diphenylsilanediyl(2-methylindenyl)(2-methyl-4-(8-quinolyl)indenyl)zirconium dichloride,
1,2-ethanediyl(2-methylindenyl)(2-methyl-4-(8-quinolyl) indenyl)zirconium dichloride,
bis(2-methyl-4,5-(2-azabenzo) indenyl) zirconium dichloride,
dimethylsilanediylbis(4,5-(2-azabenzo)indenyl)zirconium dichloride,
dimethylsilanediylbis(2-n-butyl-4,5-(2-azabenzo)indenyl) hafnium dichloride,
bis(2-i-propyl-4,5-(2-azabenzo)indenyl)zirconium dichloride,
bis(2-phenyl-4,5-(2-azabenzo)indenyl)zirconium dichloride,
bis(2-trimethylsilyl-4,5-(2-azabenzo)indenyl)zirconium dichloride,
methylphenylsilanediylbis(4,5-(2-azabenzo)indenyl) zirconium dichloride,
diphenylsilanediylbis(4,5-(2-azabenzo)indenyl)zirconium dichloride,
1,2-ethanediylbis(4,5-(2-azabenzo)indenyl)zirconium dichloride,
dimethylsilanediyl(2-methyl-4-phenylindenyl)(2-methyl-4-(4-pyridyl)indenyl)zirconium dichloride,
dimethylsilanediyl(2-methyl-4-phenylindenyl)(2-ethyl-4,5-(4-pyridyl)indenyl)zirconium dichloride,
dimethylsilanediyl(2-methyl-4-phenylindenyl)(2-n-butyl-4,5-(4-pyridyl)indenyl)zirconium dichloride,
dimethylsilanediyl(2-methyl-4-phenylindenyl)(2-i-propyl-4,5-(4-pyridyl)indenyl)zirconium dichloride,
dimethylsilanediyl(2-methyl-4-phenylindenyl)(2-phenyl-4,5-(4-pyridyl)indenyl)zirconium dichloride,
dimethylsilanediyl(2-methyl-4-phenylindenyl)(2-trimethylsilyl-4,5-(4-pyridyl)indenyl)zirconium dichloride,
methylphenylsilanediyl(2-methyl-4-phenylindenyl)-(2-methyl-4,5-(4-pyridyl)indenyl)zirconium dichloride,
diphenylsilanediyl(2-methyl-4-phenylindenyl)(2-methyl-4,5-(4-pyridyl)indenyl)zirconium dichloride,
1,2-ethanediyl(2-methyl-4-phenylindenyl)(2-methyl-4,5-(4-pyridyl)indenyl)zirconium dichloride,
dimethylsilanediyl(cyclopentadienyl)(2-methyl-4-(5-pyrimidyl)indenyl)zirconium dichloride,
dimethylsilanediyl(cyclopentadienyl)(2-ethyl-4,5-(5-pyrimidyl)indenyl)zirconium dichloride,
dimethylsilanediyl(cyclopentadienyl)(2-n-butyl-4,5-(5-pyrimidyl)indenyl)zirconium dichloride,
dimethylsilanediyl(cyclopentadienyl)(2-i-propyl-4,5-(5-pyrimidyl)indenyl)zirconium dichloride,
dimethylsilanediyl(cyclopentadienyl)(2-phenyl-4,5-(5-pyrimidyl)indenyl)zirconium dichloride,
dimethylsilanediyl(cyclopentadienyl)(2-trimethylsilyl-4,5-(5-pyrimidyl)indenyl)zirconium dichloride,
methylphenylsilanediyl(cyclopentadienyl)(2-methyl-4,5-(5-pyrimidyl)indenyl)zirconium dichloride,
diphenylsilanediyl(cyclopentadienyl)(2-methyl-4,5-(5-pyrimidyl)indenyl)zirconium dichloride,
1,2-ethanediyl(cyclopentadienyl)(2-methyl-4,5-(5-pyrimidyl)indenyl)zirconium dichloride,
dimethylsilanediyl(2-methyl-4,5-benzoindenyl)(2-methyl-4-(2-furanyl)indenyl)zirconium dichloride,
dimethylsilanediyl(2-methyl-4,5-benzoindenyl)(2-ethyl-4,5-(2-furanyl)indenyl)zirconium dichloride,
dimethylsilanediyl(2-methyl-4,5-benzoindenyl)(2-n-butyl-4,5-(2-furanyl)indenyl)zirconium dichloride,
dimethylsilanediyl(2-methyl-4,5-benzoindenyl)(2-i-propyl-4,5-(2-furanyl)indenyl)zirconium dichloride,
dimethylsilanediyl(2-methyl-4,5-benzoindenyl)(2-phenyl-4,5-(2-furanyl)indenyl)zirconium dichloride,
dimethylsilanediyl(2-methyl-4,5-benzoindenyl)(2-trimethylsilyl-4,5-(2-furanyl)indenyl)zirconium dichloride,
methylphenylsilanediyl(2-methyl-4,5-benzoindenyl)(2-methyl-4,5-(2-furanyl)indenyl)zirconium dichloride,
diphenylsilanediyl(2-methyl-4,5-benzoindenyl)(2-methyl-4,5-(2-furanyl)indenyl)zirconium dichloride,
1,2-ethanediyl(2-methyl-4,5-benzoindenyl)(2-methyl-4,5-(2-furanyl)indenyl)zirconium dichloride,
dimethylsilanediyl(2-methyl-4-phenylindenyl)(2-methyl-4-(2-fufuryl)indenyl)zirconium dichloride,
dimethylsilanediyl(2-methyl-4-phenylindenyl)(2-ethyl-4,5-(2-fufuryl)indenyl)zirconium dichloride,
dimethylsilanediyl(2-methyl-4-phenylindenyl)(2-n-butyl-4,5-(2-fufuryl)indenyl)zirconium dichloride,
dimethylsilanediyl(2-methyl-4-phenylindenyl)(2-i-propyl-4,5-(2-fufuryl)indenyl)zirconium dichloride,
dimethylsilanediyl(2-methyl-4-phenylindenyl)(2-phenyl-4,5-(2-fufuryl)indenyl)zirconium dichloride,
dimethylsilanediyl(2-methyl-4-phenylindenyl)(2-trimethylsilyl-4,5-(2-fufuryl)indenyl)zirconium dichloride,
methylphenylsilanediyl(2-methyl-4-phenylindenyl)-(2-methyl-4,5-(2-fufuryl)indenyl)zirconium dichloride,
diphenylsilanediyl(2-methyl-4-phenylindenyl)(2-methyl-4,5-(2-fufuryl)indenyl)zirconium dichloride,
1,2-ethanediyl(2-methyl-4-phenylindenyl)(2-methyl-4,5-(2-fufuryl)indenyl)zirconium dichloride,
dimethylsilanediyl(methylcyclopentadienyl)(2-methyl-4,6-bis(2-pyridyl)indenyl)zirconium dichloride,
dimethylsilanediyl(methylcyclopentadienyl)(2-ethyl-4,6-bis(2-pyridyl)indenyl)zirconium dichloride,
dimethylsilanediyl(methylcyclopentadienyl)(2-n-butyl-4,6-bis(2-pyridyl)indenyl)zirconium dichloride,
dimethylsilanediyl(methylcyclopentadienyl)(2-i-propyl-4,6-bis(2-pyridyl)indenyl)zirconium dichloride,
dimethylsilanediyl(methylcyclopentadienyl)(2-phenyl-4,6-bis(2-pyridyl)indenyl)zirconium dichloride,
dimethylsilanediyl(methylcyclopentadienyl)(2-trimethylsilyl-4,6-bis(2-pyridyl)indenyl)zirconium dichloride, methylphenylsilanediyl(methylcyclopentadienyl)(2-methyl-4,6-bis(2-pyridyl)indenyl)zirconium dichloride,
diphenylsilanediyl(methylcyclopentadienyl)(2-methyl-4,6-bis(2-pyridyl)indenyl)zirconium dichloride,
1,2-ethanediyl(methylcyclopentadienyl)(2-methyl-4,6-bis(2-pyridyl)indenyl)zirconium dichloride,
dimethylsilanediyl(fluorenyl)(2-methyl-4-(3-quinolyl)indenyl)zirconium dichloride,
dimethylsilanediyl(fluorenyl)(2-ethyl-4-(3-quinolyl)indenyl)zirconium dichloride,
dimethylsilanediyl(fluorenyl)(2-n-butyl-4-(3-quinolyl)indenyl)zirconium dichloride,
dimethylsilanediyl(fluorenyl)(2-i-propyl-4-(3-quinolyl)indenyl)zirconium dichloride,
dimethylsilanediyl(fluorenyl)(2-phenyl-4-(3-quinolyl)indenyl)zirconium dichloride,
dimethylsilanediyl(fluorenyl)(2-trimethylsilyl-4-(3-quinolyl)indenyl)zirconium dichloride,
methylphenylsilanediyl(fluorenyl)(2-methyl-4-(3-quinolyl)indenyl)zirconium dichloride,
diphenylsilanediyl(fluorenyl)(2-methyl-4-(3-quinolyl)indenyl)zirconium dichloride,
1,2-ethanediyl(fluorenyl)(2-methyl-4-(3-quinolyl)indenyl)zirconium dichloride,
dimethylsilanediylbis(2-methyl-6-(8-quinolyl)indenyl)zirconium dichloride,
dimethylsilanediylbis(2-ethyl-6-(8-quinolyl)indenyl)zirconium dichloride,
dimethylsilanediylbis(2-n-butyl-6-(8-quinolyl)indenyl)zirconium dichloride,
dimethylsilanediylbis(2-i-propyl-6-(8-quinolyl)indenyl)zirconium dichloride,
dimethylsilanediylbis(2-phenyl-6-(8-quinolyl)indenyl)zirconium dichloride,
dimethylsilanediylbis(2-trimethylsilyl-6-(8-quinolyl)indenyl)zirconium dichloride,
methylphenylsilanediylbis(2-methyl-6-(8-quinolyl)indenyl)zirconium dichloride,
diphenylsilanediylbis(2-methyl-6-(8-quinolyl)indenyl)zirconium dichloride,
1,2-ethanediylbis(2-methyl-6-(8-quinolyl)indenyl)zirconium dichloride,
dimethylsilanediyl(methylcyclopentadienyl)(2-methyl-4,5-(2-azabenzo)indenyl)zirconium dichloride,
dimethylsilanediyl(methylcyclopentadienyl)(2-ethyl-4,5-(2-azabenzo)indenyl)zirconium dichloride
dimethylsilanediyl(methylcyclopentadienyl)(2-n-butyl-4,5-(2-azabenzo)indenyl)zirconium dichloride,
dimethylsilanediyl(methylcyclopentadienyl)(2-i-propyl-4,5-(2-azabenzo)indenyl)zirconium dichloride,
dimethylsilanediyl(methylcyclopentadienyl)(2-phenyl-4,5-(2-azabenzo)indenyl)zirconium dichloride,
dimethylsilanediyl(methylcyclopentadienyl)(2-trimethylsilyl-4,5-(2-azabenzo)indenyl)zirconium dichloride,
methylphenylsilanediyl(methylcyclopentadienyl)(2-methyl-4,5-(2-azabenzo)indenyl)zirconium dichloride,
diphenylsilanediyl(methylcyclopentadienyl)(2-methyl-4,5-(2-azabenzo)indenyl)zirconium dichloride,
1,2-ethanediyl(methylcyclopentadienyl)(2-methyl-4,5-(2-azabenzo)indenyl)zirconium dichloride,
dimethylsilanediylbis((4-pyridyl)cyclopentadienyl)zirconium dichloride,
dimethylsilanediylbis(ethyl-(4-pyridyl)cyclopentadienyl)zirconium dichloride,
dimethylsilanediylbis(n-butyl-(4-pyridyl)cyclopentadienyl)zirconium dichloride,
dimethylsilanediylbis(i-propyl-(4-pyridyl)cyclopentadienyl)zirconium dichloride,
dimethylsilanediylbis(phenyl-(4-pyridyl)cyclopentadienyl)zirconium dichloride,
dimethylsilanediylbis(trimethylsilyl-(4-pyridyl)cyclopentadienyl)zirconium dichloride,
methylphenylsilanediylbis(methyl-(4-pyridyl)cyclopentadienyl)zirconium dichloride,
diphenylsilanediylbis((4-pyridyl)cyclopentadienyl)zirconium dichloride,
1,2-ethanediylbis((4-pyridyl)cyclopentadienyl)zirconium dichloride,
dimethylsilanediyl(cyclopentadienyl)(4-(5-pyrimidyl)cyclopentadienyl)zirconium dichloride,
(cyclopentadienyl)((5-pyrimidyl)cyclopentadienyl)zirconium dichloride,
dimethylsilanediyl(methylcyclopentadienyl)(n-butyl(5-pyrimidyl)cyclopentadienyl)zirconium dichloride.

The metallocenes of the formula I are prepared by methods known in the literature (Chem. Lett., 1991, 11, p. 2047 ff).

Bridged metallocenes of the formula II can, for example, be prepared according to the following reaction scheme:

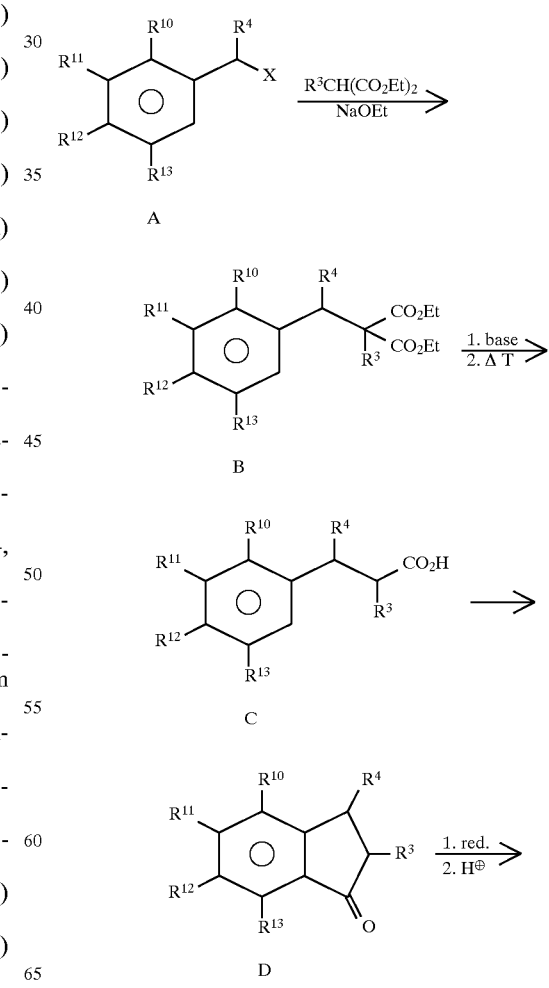

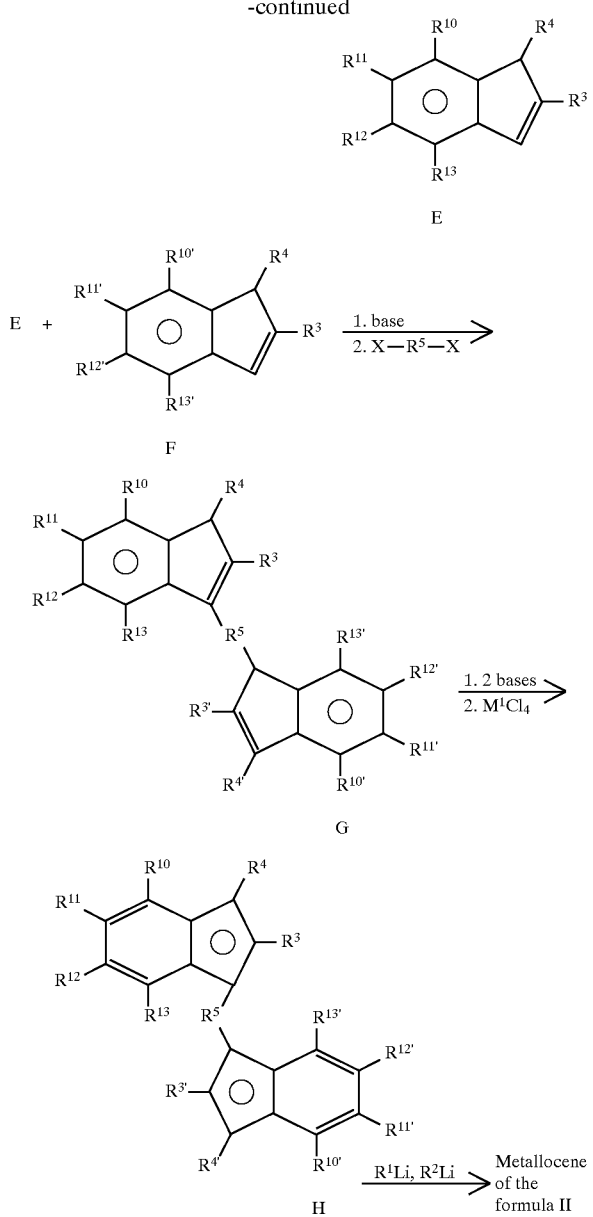

The benzyl halide derivatives of the formula A are commercially available or can be prepared by methods known in the literature.

The conversion to the compounds of the formula B is carried out by reaction with substituted malonic esters under basic conditions, for example in ethanolic solutions of sodium ethoxide.

The compounds of the formula B are saponified using alkali metal hydroxides such as potassium hydroxide or sodium hydroxide and the dicarboxylic acids formed are decarboxylated by thermal treatment to give the compounds of the formula C.

The ring closure to give the corresponding indanones of the formula D is carried out by reaction with chlorinating agents such as $SOCl_2$ to form the corresponding acid chlorides and subsequent cyclization with a Friedel-Crafts catalyst in an inert solvent, for example $AlCl_3$ or polyphosphoric acid in methylene chloride or $CS_2$.

The conversion to the indene derivatives of the formula E is carried out by reduction with a hydride-transferring reagent such as sodium borohydride or lithium aluminum hydride or hydrogen and an appropriate catalyst in an inert solvent such as diethyl ether or tetrahydrofuran to form the corresponding alcohols and dehydration of the alcohols under acid conditions, for example using p-toluenesulfonic acid or an aqueous mineral acid or by reaction with water-withdrawing substances such as magnesium sulfate, anhydrous copper sulfate or molecular sieves.

The preparation of the ligand systems of the formula G and the conversion to the bridged chiral metallocenes of the formula H, as well as the isolation of the desired racemic forms, are known in principle. For this purpose, the indene derivative of the formula E is deprotonated with a strong base such as butyllithium or potassium hydride in an inert solvent and reacted with a reagent of the formula F to form the ligand system of the formula G. This is subsequently deprotonated with two equivalents of a strong base such as butyllithium or potassium hydride in an inert solvent and reacted with the corresponding metal tetrahalide such as zirconium tetrachloride in a suitable solvent. Suitable solvents are aliphatic or aromatic solvents such as hexane or toluene, ether solvents such as tetrahydrofuran or diethyl ether or halogenated hydrocarbons such as methylene chloride or halogenated aromatic hydrocarbons such as o-dichlorobenzene. The separation of the racemic and the meso form is carried out by extraction or recrystallization using suitable solvents.

Metallocenes of the formula I can also be obtained by direct reaction of the ligand system of the formula G with a reagent of the formula $M^1NR^6{}_2)_4$. It is here possible to influence the formation of the racemic and the meso form (Organometallics, 1995, 14, 5–7).

Derivative formation to give the metallocenes of the formula II can be carried out, for example, by reaction with alkylating agents such as methyllithium.

The present invention also provides a process for preparing a polyolefin by polymerization of at least one olefin in the presence of a catalyst comprising at least one metallocene compound and at least one cocatalyst, wherein the metallocene is a compound of the formula I, preferably of the formula II. For the purposes of the present invention, the term polymerization covers both a homopolymerization and a copolymerization.

Preference is given to homopolymerizing or copolymerizing olefins of the formula $R^a$—CH=CH—$R^b$, where $R^a$ and $R^b$ are identical or different and are each a hydrogen atom or a hydrocarbon radical having from 1 to 20 carbon atoms, in particular from 1 to 10 carbon atoms, or $R^a$ and $R^b$ together with the atoms connecting them form one or more rings. Examples of such olefins are 1-olefins such as ethylene, propylene, 1-butene, 1-pentene, 1-hexene, 4-methyl-1-pentene or 1-octene, styrene, dienes such as 1,3-butadiene or 1,4-hexadiene and cyclic olefins such as norbornene, tetracyclododecene, norbornadiene or vinylnorbornene. In the process of the invention, preference is given to homopolymerizing ethylene or propylene or copolymerizing or ethylene with one or more 1-olefins having from 3 to 20 carbon atoms, for example propylene, and/or one or more dienes having from 4 to 20 carbon atoms, for example 1,4-butadiene. Examples of such copolymers are ethylene-propylene copolymers and ethylene-propylene-1,4-hexadiene copolymers.

The polymerization is preferably carried out at a temperature of from −60° to 250° C., particularly preferably from 50° to 200° C. The pressure is preferably from 0.5 to 2000 bar, particularly preferably from 5 to 64 bar.

The polymerization can be carried out in solution, in bulk, in suspension or in the gas phase, continuously or batchwise, and in one or more stages. A preferred embodiment is gas-phase polymerization.

The catalyst used in the process of the invention preferably comprises one metallocene compound of the formula I. It is also possible to use mixtures of two or more metallocene compounds of the formula I, or mixtures of metallocene compounds of the formula I with other metallocenes or semi-sandwich compounds, e.g. for preparing polyolefins having a broad or multimode molecular weight distribution.

The chiral metallocenes of the formula I are preferably used as racemate. However, it is also possible to use the pure enantiomer in the (+) or (−) form. An optically active polymer can be prepared using the pure enantiomers. However, the meso form of the metallocenes should be removed, since the polymerization-active center (the metal atom) in these compounds is no longer chiral because of the mirror symmetry at the central metal atom and can therefore not produce a highly isotactic polymer. If the meso form is not removed, atactic polymer is formed in addition to isotactic polymers. For certain applications, for example flexible moldings, this can be quite desirable.

According to the invention, use is made of at least one cocatalyst which is preferably an aluminum compound and/or a boron compound. The aluminum compound is preferably an aluminoxane, in particular of the formula IIa for the linear type and/or of the formula IIb for the cyclic type

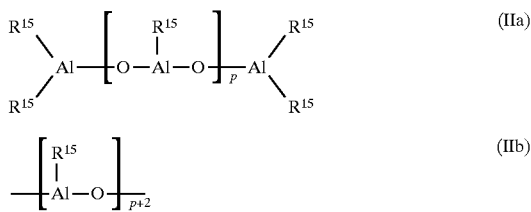

where, in the formulae IIa and IIb, the radicals $R^{15}$ can be identical or different and are each hydrogen or a $C_1$–$C_{20}$-hydrocarbon group such as a $C_1$–$C_6$-alkyl group, a $C_6$–$C_{18}$-aryl group or benzyl, and p is an integer from 2 to 50, preferably from 10 to 35.

The radicals $R^{15}$ are preferably identical and are methyl, isobutyl, phenyl or benzyl, particularly preferably methyl.

If the radicals $R^{15}$ are different, they are preferably methyl and hydrogen or alternatively methyl and isobutyl, with hydrogen or isobutyl preferably being present in an amount of from 0.01 to 40% (number of the radicals $R^{15}$).

The aluminoxane can be prepared in various ways by known methods. One of the methods is, for example, reacting an aluminum-hydrocarbon compound and/or a hydridoaluminum-hydrocarbon compound with water (gaseous, solid, liquid or bound—for example as water of crystallization) in an inert solvent (for example toluene). To prepare an aluminoxane having different radicals $R^{15}$, for example, two different trialkylaluminums corresponding to the desired composition are reacted with water Regardless of the way in which they are prepared, all aluminoxane solutions have in common a varying content of unreacted aluminum starting compound which is present in free form or as adduct.

It is possible to preactivate the metallocene prior to use in the polymerization reaction using the cocatalyst, e.g. an aluminoxane. This significantly increases the polymerization activity and improves the particle morphology. The preactivation of the transition metal compound is carried out in solution. The metallocene is here preferably dissolved in a solution of the aluminoxane in an inert hydrocarbon. Suitable inert hydrocarbons are aliphatic or aromatic hydrocarbons. Preference is given to using toluene.

The concentration of the aluminoxane in the solution is in the range from about 1% by weight to the saturation limit, preferably from 5 to 30% by weight, in each case based on the total amount of solution. The metallocene can be used in the same concentration, but it is preferably used in an amount of $10^{-4}$–1 mol per mol of aluminoxane. The preactivation time is from 5 minutes to 60 hours, preferably from 5 to 60 minutes. The preactivation is carried out at a temperature of from −78° to 100° C., preferably from 0° to 70° C.

A prepolymerization can be carried out with the aid of the metallocene. For the prepolymerization, preference is given to using the (or one of the) olefin(s) used in the polymerization.

The catalyst used in the process of the invention can be supported. Application to a support enables, for example, the particle morphology of the polyolefin prepared to be controlled. Here, the metallocene compound can first be reacted with the support and subsequently with the cocatalyst, the cocatalyst can also first be supported and subsequently reacted with the metallocene compound. It is also possible to support the reaction product of metallocene compound and cocatalyst. Suitable support materials are, for example, silica gels, aluminum oxides, solid aluminoxane or other inorganic support materials such as magnesium chloride. Another suitable support material is a polyolefin powder in finely divided form.

Preferably, the cocatalyst, i.e. the organoaluminum compound, is applied to a support such as silica gel, aluminum oxide, solid aluminoxane, another inorganic support material or a polyolefin powder in finely divided form and then reacted with the metallocene.

Inorganic supports which can be used are oxides which are produced flame-pyrolytically by combustion of element halides in a hydrogen/oxygen flame, or can be prepared as silica gels in certain particle size distributions and particle shapes.

The preparation of the supported cocatalyst can be carried out, for example as described in EP 92 107 331.8, in the following manner in a stainless steel reactor having an explosion-proof design and provided with a pumped circulation system rated for 60 bar, inert gas supply, heating by jacket cooling and a second cooling circuit via a heat exchanger on the pumped circulation system. The pumped circulation system sucks in the reactor contents via a connection in the bottom of the reactor by means of a pump and pumps it into a mixer and through a rising line via a heat exchanger back into the reactor. The mixer is configured in such a way that in the inlet there is a constricted pipe cross section where an increased flow velocity occurs and into whose turbulent zone there is led, axially and opposite the flow direction, a thin feed line through which—pulsed—a defined amount of water can be fed in under 40 bar of argon. The reaction is monitored via a sampler on the pumped circuit.

However, other reactors are also suitable in principle.

The abovedescribed reactor having a volume of 16 dm³ is charged with 5 dm³ of decane under inert conditions. 0.5 dm³ (=5.2 mol) of trimethylaluminum are added at 25° C. Subsequently, 250 g of silica gel SD 3216-30 (Grace AG), which have previously been dried at 120° C. in an argon fluidized bed, are introduced into the reactor through a solids funnel and homogeneously distributed by means of the stirrer and the pumped circulation system. A total amount of 76.5 g of water is added to the reactor in portions of 0.1 cm³ every 15 seconds over a period of 3.25 hours. The pressure, caused by the argon and the gases formed, is kept constant at 10 bar by means of a pressure regulating valve. After all the water has been introduced, the pumped circulation system is switched off and the stirring is continued for a further 5 hours at 25° C.

The supported cocatalyst prepared in this manner is used as a 10% strength suspension in n-decane. The aluminum content is 1.06 mmol of Al per cm$^3$ of suspension. The isolated solid contains 31% by weight of aluminum, the suspension medium contains 0.1% by weight of aluminum.

Further possible ways of preparing a supported cocatalyst are described in EP 92 107331.8.

The metallocene of the invention is subsequently applied to the supported cocatalyst by stirring the dissolved metallocene with the supported cocatalyst. The solvent is removed and replaced by a hydrocarbon in which both the cocatalyst and the metallocene are insoluble.

The reaction to form the supported catalyst system is carried out at a temperature of from −20° to +120° C., preferably from 0° to 100° C., particularly preferably at from 15° to 40° C. The metallocene is reacted with the supported cocatalyst by combining the cocatalyst as a 1–40% strength by weight suspension, preferably a 5–20% strength by weight suspension, in an aliphatic, inert suspension medium such as n-decane, hexane, heptane or diesel oil with a solution of the metallocene in an inert solvent such as toluene, hexane, heptane or dichloromethane or with the finely milled solid metallocene. Alternatively, a solution of the metallocene can also be reacted with the solid cocatalyst.

The reaction is carried out by intensive mixing, for example by stirring, at a molar Al/M$^1$ ratio of from 100/1 to 10000/1, preferably from 100/1 to 3000/1, and a reaction time of from 5 to 120 minutes, preferably from 10 to 60 minutes, particularly preferably from 10 to 30 minutes, under inert conditions.

During the course of the reaction time for preparing the supported catalyst system, changes occur in the color of the reaction mixture, particularly when using metallocenes of the invention having absorption maxima in the visible region, and the progress of the reaction can be followed by these color changes.

After the end of the reaction time, the supernatant solution is removed, for example by filtration or decantation. The remaining solid is washed from 1 to 5 times with an inert suspension medium such as toluene, n-decane, hexane, diesel oil or dichloromethane for removing soluble constituents in the catalyst formed, in particular for removing unreacted and therefore soluble metallocene.

The supported catalyst system thus prepared can be introduced into the polymerization system as powder dried in vacuo or resuspended while still moist with solvent and introduced as a suspension in one of the above-mentioned inert suspension media.

According to the invention, boron compounds, in particular those of the formulae $R^{16}_x NH_{4-x} BR^{17}_4$, $R^{16}_x PH_{4-x} BR^{17}_4$, $R^{16}_3 CBR^{17}_4$, $BR^{17}_3$, can also be used as cocatalysts. In these formulae, x is a number from 1 to 4, preferably 3, the radicals $R^{16}$ are identical or different, preferably identical, and are $C_1$–$C_{10}$-alkyl, $C_6$–$C_{18}$-aryl or 2 radicals $R^{16}$ together with the atom connecting them form a ring, and the radicals $R^{17}$ are identical or different, preferably identical, and are $C_6$–$C_{18}$-aryl which can be substituted by alkyl, haloalkyl or fluorine.

In particular, $R^{16}$ is ethyl, propyl, butyl or phenyl and $R^{17}$ is phenyl, pentafluorophenyl, 3,5-bistrifluoromethylphenyl, mesityl, xylyl or tolyl (cf. EP 277 003, EP 277 004 and EP 426 638).

When using the abovementioned cocatalysts, the actual (active) polymerization catalyst consists of the reaction product of metallocene and one of the specified compounds. For this reason, this reaction product is preferably first prepared outside the polymerization reactor in a separate step using a suitable solvent.

According to the invention, suitable cocatalysts are in principle any compounds which, owing to their Lewis acidity, can convert the neutral metallocene into a cation and stabilize the latter ("labile coordination"). Furthermore, the cocatalyst or the anion formed therefrom should undergo no further reactions with the metallocene cation formed (cf. EP 427 697).

To remove catalyst poisons present in the olefin, purification using an aluminum alkyl, for example trimethylaluminum, triethylaluminum or triisobutylaluminum, is advantageous. This purification can be carried out either in the polymerization system itself or the olefin is, prior to addition to the polymerization system, brought into contact with the Al compound and subsequently separated off again.

As molecular weight regulator and/or to increase the activity, hydrogen is added if necessary. The total pressure in the polymerization system is from 0.5 to 100 bar. Preference is given to polymerization in the industrially particularly interesting pressure range of from 5 to 64 bar.

The metallocene is here used in a concentration, based on the transition metal, of from $10^{-3}$ to $10^{-8}$ mol, preferably from $10^{-4}$ to $10^{-7}$ mol, of transition metal per dm$^3$ of solvent or per dm$^3$ of reactor volume. The aluminoxane is used in a concentration of from $10^{-5}$ to $10^{-1}$ mol, preferably from $10^{-4}$ to $10^{-2}$ mol, per dm$^3$ of solvent or per dm$^3$ of reactor volume. The other cocatalysts mentioned are used in approximately equimolar amounts to the metallocene. However, higher concentrations are also possible in principle.

If the polymerization is carried out as a suspension or solution polymerization, an inert solvent customary for the Ziegler low-pressure process is used. For example, the polymerization is carried out in an aliphatic or cycloaliphatic hydrocarbon, examples which may be mentioned being propane, butane, hexane, heptane, isooctane, cyclohexane, methylcyclohexane. It is also possible to use a petroleum or hydrogenated diesel oil fraction. Toluene can also be used. Preference is given to carrying out the polymerization in the liquid monomer.

If inert solvents are used, the monomers are metered in in gaseous or liquid form.

The polymerization time can be any desired, since the catalyst system to be used according to the invention shows only a slight time-dependent decrease in the polymerization activity.

Before addition of the catalyst, in particular the supported catalyst system (comprising a metallocene of the invention and a supported cocatalyst or comprising a metallocene of the invention and an organoaluminum compound on a polyolefin powder in finely divided form), another aluminum alkyl compound such as trimethylaluminum, triethylaluminum, triisobutylaluminum, trioctylaluminum or isoprenylaluminum can be additionally added to the reactor to make the polymerization system inert (for example for removing any catalyst poisons in the olefin, viz. as scavenger). This is added to the polymerization system in a concentration of from 100 to 0.01 mmol of Al per kg of reactor contents. Preference is given to triisobutylaluminum and triethylaluminum in a concentration of from 10 to 0.1 mmol of Al per kg of reactor contents. This enables a small molar ratio of Al/M$^1$ to be selected in the synthesis of a supported catalyst system.

The following examples illustrate the invention.

All glass apparatus was baked out in vacuo and flushed with argon. All operations were carried out with exclusion of moisture and oxygen in Schlenk vessels. The solvents used were in each case freshly distilled from Na/K alloy under argon and stored in Schlenk vessels.

The Al/CH$_3$ ratio in the aluminoxane was determined by decomposing the sample with H$_2$SO$_4$ and determining the volume of the hydrolysis gases formed under standard conditions and by complexometric titration of the aluminum in the then dissolved sample by the Schwarzenbach method.

For the examples, toluene-soluble methylaluminoxane was employed for the suspension polymerization and for the bulk polymerization using unsupported metallocene as a 10% strength by weight toluene solution and, according to aluminum determination, contained 36 mg of Al/cm$^3$. The mean degree of oligomerization according to freezing point lowering in benzene was n=20. For the toluene-soluble methylaluminoxane, an Al:CH$_3$ ratio of 1:1.55 was determined.

Definitions

VZ=Viscosity number in cm$^3$/g
M$_w$=Weight average molecular weight in g/mol (determined by gel permeation chromatography)
M$_w$/M$_n$=Polydispersity
mp.=Melting point in °C. (determined by DSC, 20° C./min heating and cooling rate)
II=Isotactic index (II=mm+½ mr, determined by $^{13}$C-NMR spectroscopy)
MFI 230/5=Melt flow index, measured in accordance with DIN 53735; in dg/min
BD=Polymer bulk density in g/dm$^3$.

A. Dimethylsilanediylbis(2-methyl-4-(2-pyridyl)indenyl)zirconium Dichloride (1)

1. 2-(2-(2-Pyridyl)benzyl)propionic Acid 148 g (0.85 mol) of diethyl methylmalonate were added dropwise at room temperature to 19.5 g (0.85 mol) of sodium in 400 cm$^3$ of H$_2$O-free EtOH. Subsequently, 211 g (0.85 mol) of 2-(2-pyridyl)benzyl bromide were added dropwise and the mixture was heated under reflux for 3 hours. At room temperature, 143 g (2.55 mol) of KOH dissolved in 500 cm$^3$ of H$_2$O were added and the mixture was heated under reflux for a further 4 hours. The EtOH was distilled off and the residue was admixed with H$_2$O until completely dissolved and subsequently acidified with concentrated aqueous HCl to a pH of 1. The precipitate formed was filtered off with suction, dried and heated for 1 hour at 130° C. This gave 193 g (94%) of 2-(2-(2-pryridyl)benzyl)propionic acid as solid.

2. 2-Methyl-4-(2-pyridyl)-1-indanone

A solution of 193 g (0.80 mol) of 2-(2-(2-(pyridyl)benzyl)propionic acid in 81 cm$^3$ (1.2 mol) of thionyl chloride was stirred at room temperature for 18 hours. Excess thionyl chloride was removed at 10 mbar and the acid chloride was taken up in 400 cm$^3$ of toluene. The solution was added dropwise at 10° C. to a suspension of 113 g (0.85 mol) of AlCl$_3$ in 1500 cm$^3$ of toluene and heated at 80° C. for 1 hour. The reaction mixture was poured onto 2000 g of ice and acidified with concentrated aqueous HCl to a pH of 1. The organic phase was separated off and the aqueous phase was further extracted 3 times with 200 cm$^3$ each time of Et$_2$O. The combined organic phases were washed with saturated aqueous NaHCO$_3$ solution and saturated aqueous NaCl solution and subsequently dried (MgSO$_4$). This gave 132 g (74%) of 2-methyl-4-(2-pyridyl)-1-indanone which was further reacted without further purification.

3. 2-Methyl-7-(2-pyridyl)indene 24.6 g (0.65 mol) of NaBH, were added in portions at 0° C. to a solution of 132 g (0.59 mol) of 2-methyl-4-(2-pyridyl)-1-indanone in 1000 cm$^3$ of THF/methanol 2:1 and the mixture was stirred for 18 hours at room temperature. The reaction mixture was poured onto 1000 g of ice, admixed with concentrated aqueous HCl to a pH of 1 and extracted a number of times with Et$_2$O. The combined organic phases were washed with saturated aqueous NaHCO$_3$ solution and saturated aqueous NaCl solution. The solvent was removed under reduced pressure and the crude product was taken up in 1000 cm$^3$ of toluene, admixed with 4.5 g of p-toluenesulfonic acid and heated under reflux for 2 hours using a water separator. Distillation at 0.1 mbar and 145° C. gave 84 g (69%) of 2-methyl-7-(2-pyridyl)indene as a colorless oil.

4. Dimethylbis(2-methyl-4-(2-pyridyl)indenyl)silane

A solution of 25 g (120 mmol) of 2-methyl-7-(2-pyridyl)indene in 250 cm$^3$ of anhydrous, O$_2$-free toluene and 25 ml of anhydrous, O$_2$-free THF was admixed at room temperature with 45 cm$^3$ (120 mmol) of a 20% strength solution of butyllithium in toluene and the mixture was heated for 2 hours at 80° C. Subsequently, the yellow suspension was cooled to 0° C. and admixed with 7.7 g (60 mmol) of dimethyldichlorosilane. The reaction mixture was heated for a further 1 hour at 80° C. and subsequently washed with 200 cm$^3$ of H$_2$O. The solvent was removed under reduced pressure and the residue was purified by crystallization (hexane). This gave 14.9 g (53%) of dimethylbis(2-methyl-4-(2-pyridyl)indenyl)silane as a colorless solid.

5. Dimethylsilanediylbis(2-methyl-4-(2-pyridyl)indenyl)zirconium Dichloride (1)

A solution of 5 g (10.6 mmol) of dimethylbis(2-methyl-4-(2-pyridyl)indenyl)silane in 50 cm$^3$ of anhydrous, O$_2$-free Et$_2$O was admixed under argon at room temperature with 8 cm$^3$ of a 20% strength solution of butyllithium in toluene and the mixture was subsequently heated under reflux for 3 hours. The solvent was removed under reduced pressure and the residue together with 50 ml of anhydrous, O$_2$-free hexane was filtered through a G3 Schlenk frit, washed with 50 ml of anhydrous, O$_2$-free hexane and dried (0.1 mbar, RT). The solid was added at −78° C. to a suspension of 2.3 g (10 mmol) of zirconium tetrachloride in 50 cm$^3$ of methylene chloride and warmed to room temperature over the course of 18 hours with magnetic stirring. The mixture was filtered through a G3 frit and the residue was extracted with portions of methylene chloride, using a total of 100 cm$^3$ of methylene chloride. The combined filtrates were freed of the solvent under reduced pressure and again recrystallized from methylene chloride. This gave 1.7 g (25%) of the racemic and the meso form in a ratio of 1:1. Renewed recrystallization from toluene gave the racemic complex dimethylsilanediylbis(2-methyl-4-(2-pyridyl)indenyl)zirconium dichloride (1) in the form of yellow crystals.

$^1$H-NMR (100 MHz, CDCl$_3$): 7.0–8.3 (m, 14 H, arom. H), 6.8 (s, 2H, H-C(3)), 2.2 (s, 6H, CH$_3$), 1.1 (s, 6H, CH$_3$Si). Mass spectrum: 630 M$^+$, correct desintegration pattern.

B. Dimethylsilanediylbis(2-methyl-4-(3-quinolyl)indenyl)zirconium Dichloride (2)

6. 2-(2-(3-Quinolyl)benzyl)propionic Acid 104 g (0.6 mol) of diethyl methylmalonate were added dropwise at room temperature to 13.8 g (0.6 mol) of sodium in 300 cm³ of H₂O-free EtOH. Subsequently, 178 g (0.6 mol) of 2-(3-quinolyl)benzyl bromide were added dropwise and the mixture was heated under reflux for 3 hours. At room temperature, 100 g (1.8 mol) of KOH dissolved in 400 cm³ of H₂O were added and the mixture was heated under reflux for a further 4 hours. The EtOH was distilled off and the residue was admixed with H₂O until completely dissolved and subsequently acidified with concentrated aqueous HCl to a pH of 1. The precipitate formed was filtered off with suction, dried and heated for 1 hour at 130° C. This gave 145 g (83%) of 2-(2-(3-quinolyl)benzyl)propionic acid as solid.

7. 2-Methyl-4-(3-quinolyl)-1-indanone

A solution of 145 g (0.5 mol) of 2-(2-(3-quinolyl)benzyl) propionic acid in 119 g (1.0 mol) of thionyl chloride was stirred at room temperature for 18 hours. Excess thionyl chloride was removed at 10 mbar and the acid chloride was taken up in 400 cm³ of toluene. The solution was added dropwise at 10° C. to a suspension of 73 g (0.55 mol) of AlCl₃ in 1000 cm³ of toluene and heated at 80° C. for 1 hour. The reaction mixture was poured onto 1000 g of ice and acidified with concentrated aqueous HCl to a pH of 1. The organic phase was separated off and the aqueous phase was further extracted 3 times with 200 cm³ each time of Et₂O. The combined organic phases were washed with saturated aqueous NaHCO₃ solution and saturated aqueous NaCl solution and subsequently dried (MgSO₄). This gave 64 g (47%) of 2-methyl-4-(3-quinolyl)-1-indanone which was further reacted without further purification.

8. 2-Methyl-7-(3-quinolyl)indene 11.3 g (0.3 mol) of NaBH₄ were added in portions at 0° C. to a solution of 64 g (0.23 mol) of 2-methyl-4-(3-quinolyl)-1-indanone in 600 cm³ of THF/methanol 2:1 and the mixture was stirred for 18 hours at room temperature. The reaction mixture was poured onto 1000 g of ice, admixed with concentrated aqueous HCl to a pH of 1 and extracted a number of times with Et₂O. The combined organic phases were washed with saturated aqueous NaHCO₃ solution and saturated aqueous NaCl solution. The solvent was removed under reduced pressure and the crude product was taken up in 1000 cm³ of toluene, admixed with 2 g of p-toluenesulfonic acid and heated under reflux for 2 hours using a water separator. The reaction mixture was washed 3 times with 150 cm³ of saturated aqueous NaHCO₃ solution and the solvent was removed under reduced pressure. Chromatography on silica gel (hexane/ethyl acetate 20:1) gave 45 g (76%) of 2-methyl-7-(3-quinolyl)indene as a colorless oil.

9. Dimethylbis(2-methyl-4-(3-quinolyl)indenyl)silane

A solution of 45 g (174 mmol) of 2-methyl-7-(3-quinolyl) indene in 450 cm³ of anhydrous, O₂-free toluene and 45 ml of anhydrous, O₂-free THF was admixed at room temperature with 65 cm³ (174 mmol) of a 20% strength solution of butyllithium in toluene and the mixture was heated for 2 hours at 80° C. Subsequently, the yellow suspension was cooled to 0° C. and admixed with 11.2 g (87 mmol) of dimethyldichlorosilane. The reaction mixture was heated for a further 1 hour at 80° C. and subsequently washed with 400 cm³ of H₂O. The solvent was removed under reduced pressure and the residue was purified by crystallization (hexane/diethyl ether). This gave 24 g (49%) of dimethylbis (2-methyl-4-(3-quinolyl)indenyl)silane as a colorless solid.

10. Dimethylsilanediylbis(2-methyl-4-(3-quinolyl) indenyl)zirconium Dichloride (2)

A solution of 10 g (17 mmol) of dimethylbis(2-methyl-4-(3-quinolyl)indenyl)silane in 100 cm³ of anhydrous, O₂-free Et₂O was admixed under argon at room temperature with 13 cm³ of a 20% strength solution of butyllithium in toluene and the mixture was subsequently heated under reflux for 3 hours. The solvent was removed under reduced pressure and the residue together with 150 ml of anhydrous, O₂-free hexane was filtered through a G3 Schlenk frit, washed with 50 ml of anhydrous, O₂-free hexane and dried (0.1 mbar, RT). The solid was added at −78° C. to a suspension of 4.0 g (17 mmol) of zirconium tetrachloride in 100 cm³ of methylene chloride and warmed to room temperature over the course of 18 hours with magnetic stirring. The mixture was filtered through a G3 frit and the residue was extracted with portions of methylene chloride, using a total of 200 cm³ of methylene chloride. The combined filtrates were freed of the solvent under reduced pressure and again recrystallized from methylene chloride. This gave 4.2 g (34%) of the racemic and the meso form in a ratio of 1:1. Renewed recrystallization from toluene gave the racemic complex dimethylsilanediylbis(2-methyl-4-(3-quinolyl) indenyl)zirconium dichloride (2) in the form of yellow crystals.

¹H-NMR (100 MHz, CDCl₃): 7.2–8.3 (m, 18 H, arom. H), 6.6 (s, 2H, H-C(3)), 2.2 (s, 6H, CH₃), 1.2 (s, 6H, CH₃Si).
Mass spectrum: 731 M⁺, correct desintegration pattern.

We claim:

1. A metallocene compound of the formula I

$$R^5{}_n Cp^1 Cp^2 M^1 R^1 R^2 \qquad (I)$$

where

Cp¹ and Cp² are, independently of one another, identical or different and are each an unsubstituted or substituted cyclopentadienyl group, n=zero or 1, R⁵ is a bridge, M¹ is a metal of group IVb, Vb or VIb of the Periodic Table of the Elements, R¹ and R² are identical or different and are each a hydrogen atom, a C₁–C₄₀-, hydrocarbon group which optionally contains O, —OH group, halogen atom or —NR⁶₂ group where R⁶ are identical or different and are each a C₁–C₁₀-alkyl group or a C₆–C₁₄-aryl group wherein at least one of the two groups Cp¹ and Cp² is a substituted cyclopentadienyl group which bears at least one cyclic C₅–C₂₀-group containing at least one heteroatom in the ring, or which bears a fused-on C₂–C₂₀-ring system containing at least one heteroatom in the ring wherein said heteroatom is selected from the group consisting of O, N, P, Si and S.

2. The metallocene compound as claimed in claim 1, wherein the metallocene compound is of the formula II

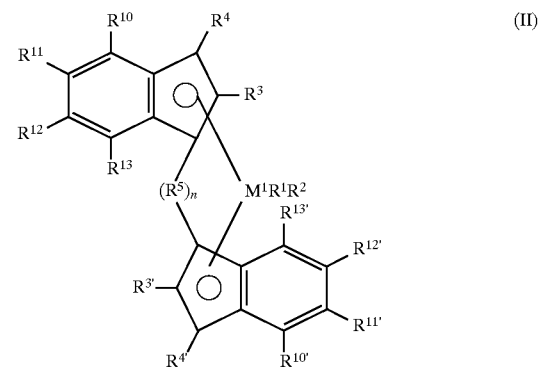

where

M¹ is a metal of group IVb, Vb or VIb of the Periodic Table of the Elements, R¹ and R² are identical or different and are each a hydrogen atom, a C₁–C₄₀- group, —OH group, halogen atom or —NR$^6{}_2$ where R$^6$ are identical or different and are each a C$_1$–C$_{10}$-alkyl group or a C$_6$–C$_{14}$-aryl group, the radicals R$^3$ and R$^{3'}$ are identical or different and are each a hydrogen atom, a halogen atom, a C$_1$–C$_{10}$-alkyl group which optionally is halogenated, a C$_6$–C$_{14}$-aryl group which optionally is halogenated, a C$_6$–C$_{14}$-aryl group which optionally is halogenated, an NR$^7{}_2$—, —SR$^7$, —OSiR$^7{}_3$, —SiR$^7{}_3$ or —PR$^7{}_2$ radical, where R$^7$ is a halogen atom, a C$_1$–C$_{10}$-alkyl group or a C$_6$–C$_{14}$-aryl group, R$^4$ and R$^{4'}$ are identical or different and are each a hydrogen atom, a halogen atom, a C$_1$–C$_{10}$-alkyl group which optionally is halogenated, a C$_6$–C$_{14}$-aryl group which can be halogenated, an —NR$^7{}_2$, —SR$^7$, —OSiR$^7{}_3$, —SiR$^7{}_3$ or —PR$^7{}_2$ radical, where R$^7$ is a halogen atom, a C$_1$–C$_{10}$-alkyl group or a C$_6$–C$_{14}$-aryl group, n=zero or 1, R$^5$ is a bridge, and R$^{10}$, R$^{11}$, R$^{12}$, R$^{13}$, R$^{10'}$, R$^{11'}$, R$^{12'}$ and R$^{13'}$ are identical or different and are each a hydrogen atom or a C$_1$–C$_{40}$-radical or two or more of the radicals R$^{10}$, R$^{11}$, R$^{12}$, R$^{13}$, R$^{10'}$, R$^{11'}$, R$^{12'}$ and R$^{13'}$ together form a C$_4$–C$_{20}$-ring system, where at least one of the radicals R$^{10}$, R$^{11}$, R$^{12}$, R$_{13}$, R$^{10'}$, R$^{11'}$, R$^{12'}$ and R$^{13'}$ is a cyclic C$_3$–C$_{30}$-hydrocarbon radical containing at least one heteroatom in the ring, or two or more of the radicals R$^{10}$, R$^{11}$, R$^{12}$, R$^{13}$, R$^{10'}$, R$^{11'}$, R$^{12'}$ and R$^{13'}$ together form a fused-on C$_2$–C$_{20}$-ring system containing at least one heteroatom in the ring wherein said heteroatom is selected from the group consisting of O, N, P, Si and S.

3. The metallocene compound as claimed in claim 2, wherein M$^1$ is titanium, zirconium, hafnium, vanadium, niobium, tantalum, chromium, molybdenum or tungsten, R$^1$ and R$^2$ are identical or different and are C$_1$–C$_{10}$-alkyl group, a C$_1$–C$_{10}$-alkoxy group, a C$_6$–C$_{14}$-aryl group, a C$_6$–C$_{10}$-aryloxy group, a C$_2$–C$_{10}$-alkenyl group, a C$_7$–C$_{40}$-arylalkyl group, a C$_7$–C$_{40}$-alkylaryl group, a C$_8$–C$_{40}$-arylalkenyl group, an —OH group, a halogen atom, or an —NR$^6{}_2$ group, wherein R$^6$ are identical or different and are a C$_1$–C$_4$-alkyl group or a C$_6$–C$_{14}$-aryl group and R$^5$ is

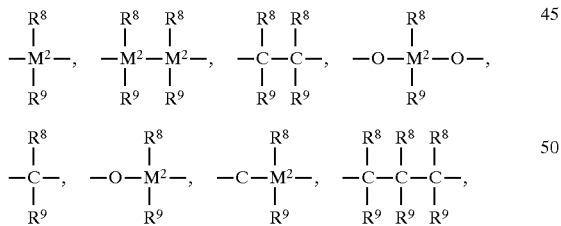

=BR$^8$, =AlR$^8$, —Ge—, —O—, —S—, =SO, =SO$_2$, =NR$^8$, =CO, =PR$^8$ or =P(O)R$^8$, where each R$^8$ and each R$^9$ is identical or different independently of the other R$^8$ and R$^9$ and is a hydrogen atom, a halogen atom, a C$_1$–C$_{10}$-alkyl group, a C$_1$–C$_{10}$-fluoroalkyl, a C$_6$–C$_{14}$-aryl group, a C$_6$–C$_{10}$-fluoroalkyl, a C$_1$–C$_{10}$-alkoxy group, a C$_2$–C$_{10}$-alkenyl group, a C$_7$–C$_{40}$-arylalkyl group, a C$_8$–C$_{40}$-arylalkenyl group or a C$_7$–C$_{40}$-alkylaryl group, or R$^8$ and R$^9$ in each case together with the atoms connecting them form one or more rings and M$^2$ is silicon, germanium or tin.

4. The metallocene compound as claimed in claim 3, wherein

M$^1$ is zirconium, hafnium or titanium,

R$^1$ and R$^2$ are identical or different and are a hydrogen atom, a C$_1$–C$_3$-alkyl group, a C$_1$–C$_3$-alkoxy group, a C$_6$–C$_{10}$-aryl group, a C$_6$–C$_8$-aryloxy group, a C$_2$–C$_4$-alkenyl group, a C$_7$–C$_{10}$-arylalkyl group, a C$_7$–C$_{11}$-alkylaryl group, a C$_6$–C$_{12}$-arylalkenyl group, an —OH group, a chlorine atom, or an —NR$^6{}_2$ where R$^6$ are identical or different and are each a C$_1$–C$_4$-alkyl group or C$_6$-aryl group, R$^8$ and R$^9$ are identical or different independently of each other and are a hydrogen atom, a halogen atom, a C$_1$–C$_4$-alkyl group, a CF$_3$ group, a C$_6$–C$_{10}$-aryl group, a pentafluorophenyl group, a C$_1$–C$_4$-alkoxy group, C$_2$–C$_4$-alkenyl group, a C$_7$–C$_{10}$-arylalkyl group, a C$_8$–C$_{12}$-arylalkenyl group or a C$_7$–C$_{12}$-alkylaryl group, M$^2$ is silicon or germanium and said at least one heteroatom in the ring is selected from the group consisting of O, N, P, Si and S which optionally bear radicals which are not constituents of the ring.

5. The metallocene compound as claimed in claim 4, wherein

R$^3$ and R$^{3'}$ are identical or different and are each a hydrogen atom, a fluorine atom, a chlorine, a bromine, a C$_1$–C$_4$-alkyl group which can be halogenated, a C$_6$–C$_{10}$-aryl group which can be halogenated, an —NR$^7{}_2$, —SR$^7$, —OSiR$^7{}_3$, —SiR$^7{}_3$ or —PR$^7{}_2$ radical, where R$^7$ is a chlorine, or a C$_1$–C$_4$-alkyl group or a group, the radicals R$^4$ and R$^{4'}$ are identical or different and are a hydrogen atom, a fluorine atom, a chlorine atom, a bromine atom, a C$_1$–C$_4$-alkyl group which can be halogenated, C$_6$–C$_{10}$-aryl group, an —NR$^7{}_2$, —SR$^7$, —OSiR$^7{}_3$, —SiR$^7{}_3$ or —PR$^7{}_2$ radical, where R$^7$ is a chlorine atom, or a C$_1$–C$_4$-alkyl group or a C$_6$–C$_{10}$-aryl group, at least one of the radicals R$^{10}$, R$^{11}$, R$^{12}$, R$^{13}$, R$^{10'}$, R$^{11'}$, R$^{12'}$, R$^{13'}$ is a cyclic C$_4$–C$_{20}$-radical containing at least one heteroatom in the ring, or two or more of the radicals R$^{10}$, R$^{11}$, R$^{12}$, R$^{13}$, R$^{10'}$, R$^{11'}$, R$^{12'}$, R$^{13'}$ together form a fused-on C$_3$–C$_{20}$ ring system containing at least one heteroatom in the ring, wherein said heteroatom is selected from the group consisting of O, N, P and S.

6. The metallocene compound as claimed in claim 2, wherein

M$^1$ is a zirconium or hafnium, the radicals R$^1$ and R$^2$ are identical or different, and are each a C$_1$–C$_4$-alkyl group, an NR$^6{}_2$ group, where R$^6$ is a C$_1$–C$_4$-alkyl radical or a halogen atom, the radicals R$^3$ and R$^{3'}$ are identical or different, and are each a C$_1$–C$_4$-alkyl group, or a C$_6$–C$_{10}$-aryl group, the radicals R$^4$ and R$^{4'}$ are identical and are each a hydrogen atom, R$^5$ is

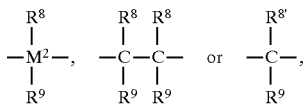

where M$^2$ is silicon or germanium and R$^8$ and R$^9$ are identical or different, and are each a C$_1$–C$_4$-alkyl, or a C$_6$–C$_{10}$-aryl group, R$^{10}$ and R$^{10'}$ are identical or different, and are each a saturated or unsaturated cyclic C$_3$–C$_{30}$-radical containing in the ring at least one heteroatom which is O, N or S which optionally bear radicals R$^{14}$ is a C$_1$–C$_4$-alkyl group, $R^{11}$, $R^{12}$, $R^{11'}$, $R^{12'}$ are identical or different, and are each a hydrogen atom, a $C_1$–$C_{10}$-radical, a $C_6$–$C_{10}$-aryl, or a saturated or unsaturated cyclic $C_3$–$C_{20}$-radical having in the ring at least one heteroatom which is O, N or S which can bear radicals $R^{14}$ wherein $R^{14}$ is a $C_1$–$C_4$-alkyl group, or at least two of the radicals $R_{10}$, $R^{11}$ and $R^{12}$ or $R^{10'}$, $R^{11'}$ and $R^{12'}$ together form a fused-on $C_2$–$C_{20}$ ring system containing at least one heteroatom in the ring, and $R^{13}$ is identical to $R^{13'}$ and is a hydrogen atom.

7. The metallocene compound as claimed in claim 6, wherein the radicals $R^1$ and $R^2$ are identical and the radicals $R^3$ and $R^{3'}$ are identical and are each a methyl, ethyl, isobutyl or phenyl, $R^8$ and $R^9$ are identical and are each a methyl, ethyl, isobutyl or phenyl, the radicals $R^{10}$ and $R^{10'}$ are identical and are each a saturated or unsaturated cyclic $C_4$–$C_{20}$-radical containing in the ring at least one heteroatom which is O, N or S which can bear radicals $R^{14}$ wherein $R^{14}$ is a $C_1$–$C_4$-alkyl group, $R^{11}$ is identical to $R^{11'}$ and $R^{12}$ is identical to $R^{12'}$, and are each a hydrogen atom, a $C_1$–$C_4$-alkyl or $C_6$–$C_{10}$-aryl, or a saturated or unsaturated cyclic $C_3$–$C_{20}$-radical having in the ring at least one heteroatom which is O, N or S which can bear radicals $R^{14}$ wherein $R^{14}$ is a $C_1$–$C_4$-alkyl group, or at least two of the radicals $R_{10}$, $R^{11}$ and $R^{12}$ or $R^{10'}$, $R^{11'}$ and $R^{12'}$ together form a fused-on $C_2$–$C_{20}$ ring system containing at least one heteroatom in the ring, and $R^{13}$ is identical to $R^{13'}$ and is a hydrogen atom.

8. The metallocene compound as claimed in claim 2, wherein $M^1$ is zirconium, $R^1$ and $R^2$ are identical and are chlorine, the radicals $R^3$ and $R^{3'}$ are identical and are each a $C_1$–$C_4$-alkyl group or a $C_6$–$C_{10}$-aryl group, $R^4$ and $R^{4'}$ are hydrogen, $R^5$ is

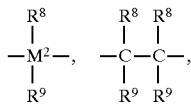

where $M^2$ is silicon, and $R^8$ and $R^9$ are identical or different and are each a $C_1$–$C_4$-alkyl group or a $C_6$–$C_{10}$-aryl group, the radicals $R_{10}$ and $R_{10'}$ are identical and are each a saturated or unsaturated cyclic $C_4$–$C_9$-radical containing at least one heteroatom selected from the group consisting of S, N, P, Si or O in the ring.

9. The metallocene compound as claimed in claim 1, wherein the metallocene is selected from the group consisting of:

dimethylsilanediylbis(2-methyl-4-(2-pyridyl)indenyl) zirconium dichloride, dimethylsilanediylbis(2-ethyl-4-(2-pyridyl)indenyl) zirconium dichloride, dimethylsilanediylbis(2-n-butyl-4-(2-pyridyl)indenyl) zirconium dichloride, dimethylsilanediylbis(2-i-propyl-4-(2-pyridyl)indenyl) zirconium dichloride, dimethylsilanediylbis(2-phenyl-4-(2-pyridyl)indenyl) zirconium dichloride, dimethylsilanediylbis(2-trimethylsilyl-4-(2-pyridyl) indenyl)zirconium dichloride, methylphenylsilanediylbis(2-methyl-4-(2-pyridyl) indenyl)zirconium dichloride, diphenylsilanediylbis(2-methyl-4-(2-pyridyl)indenyl) zirconium dichloride, 1,2-ethanediylbis(2-methyl-4-(2-pyridyl)indenyl) zirconium dichloride, dimethylsilanediylbis(2-methyl-4-(2-pyridyl)-7-methylindenyl)zirconium dichloride, dimethylsilanediylbis(2-ethyl-4-(2-pyridyl)-7-methylindenyl)zirconium dichloride, dimethylsilanediylbis(2-n-butyl-4-(2-pyridyl)-7-methylindenyl)zirconium dichloride, dimethylsilanediylbis(2-i-propyl-4-(2-pyridyl)-7-methylindenyl)zirconium dichloride, dimethylsilanediylbis(2-phenyl-4-(2-pyridyl)-7-methylindenyl)zirconium dichloride, dimethylsilanediylbis(2-trimethylsilyl-4-(2-pyridyl)-7-methylindenyl)zirconium dichloride, methylphenylsilanediylbis(2-methyl-4-(2-pyridyl)-7-methylindenyl)zirconium dichloride, diphenylsilanediylbis(2-methyl-4-(2-pyridyl)-7-methylindenyl)zirconium dichloride, 1,2-ethanediylbis(2-methyl-4-(2-pyridyl)-7-methylindenyl)zirconium dichloride, dimethylsilanediylbis(2-methyl-4-(2-pyridyl)-6-i-propylindenyl)zirconium dichloride, dimethylsilanediylbis(2-ethyl-4-(2-pyridyl)-6-i-propylindenyl)zirconium dichloride, dimethylsilanediylbis(2-n-butyl-4-(2-pyridyl)-6-i-propylindenyl)zirconium dichloride, dimethylsilanediylbis(2-i-propyl-4-(2-pyridyl)-6-i-propylindenyl)zirconium dichloride, dimethylsilanediylbis(2-phenyl-4-(2-pyridyl)-6-i-propylindenyl)zirconium dichloride, dimethylsilanediylbis(2-trimethylsilyl-4-(2-pyridyl)-6-i-propylindenyl)zirconium dichloride, methylphenylsilanediylbis(2-methyl-4-(2-pyridyl)-6-i-propylindenyl)zirconium dichloride, diphenylsilanediylbis(2-methyl-4-(2-pyridyl)-6-i-propylindenyl)zirconium dichloride, 1,2-ethanediylbis(2-methyl-4-(2-pyridyl)-6-i-propylindenyl)zirconium dichloride, dimethylsilanediylbis(2-methyl-4,6-bis(2-pyridyl) indenyl)zirconium dichloride, dimethylsilanediylbis(2-ethyl-4,6-bis(2-pyridyl)indenyl) zirconium dichloride, dimethylsilanediylbis(2-n-butyl-4,6-bis(2-pyridyl) indenyl)zirconium dichloride, dimethylsilanediylbis(2-i-propyl-4,6-bis(2-pyridyl) indenyl)zirconium dichloride, dimethylsilanediylbis(2-phenyl-4,6-bis(2-pyridyl) indenyl)zirconium dichloride, dimethylsilanediylbis(2-trimethylsilyl-4,6-bis(2-pyridyl) indenyl)zirconium dichloride, methylphenylsilanediylbis(2-methyl-4,6-bis(2-pyridyl) indenyl)zirconium dichloride, diphenylsilanediylbis(2-methyl-4,6-bis(2-pyridyl) indenyl)zirconium dichloride, 1,2-ethanediylbis(2-methyl-4,6-bis(2-pyridyl)indenyl) zirconium dichloride, dimethylsilanediylbis(2-methyl-4-(3-quinolyl)indenyl) zirconium dichloride,
dimethylsilanediylbis(2-ethyl-4-(3-quinolyl) indenyl) zirconium dichloride,
dimethylsilanediylbis(2-n-butyl-4-(3-quinolyl)indenyl) zirconium dichloride,
dimethylsilanediylbis(2-i-propyl-4-(3-quinolyl)indenyl) zirconium dichloride,
dimethylsilanediylbis(2-phenyl-4-(3-quinolyl)indenyl) zirconium dichloride,
dimethylsilanediylbis(2-trimethylsilyl-4-(3-quinolyl) indenyl)zirconium dichloride,
methylphenylsilanediylbis(2-methyl-4-(3-quinolyl) indenyl)zirconium dichloride,
diphenylsilanediylbis(2-methyl-4-(3-quinolyl)indenyl) zirconium dichloride,
1,2-ethanediylbis(2-methyl-4-(3-quinolyl)indenyl) zirconium dichloride,
dimethylsilanediylbis(2-methyl-4-(8-quinolyl)indenyl) zirconium dichloride,
dimethylsilanediylbis(2-ethyl-4-(8-quinolyl)indenyl) zirconium dichloride,
dimethylsilanediylbis(2-n-butyl-4-(8-quinolyl)indenyl) zirconium dichloride,
dimethylsilanediylbis(2-i-propyl-4-(8-quinolyl)indenyl) zirconium dichloride,
dimethylsilanediylbis(2-phenyl-4-(8-quinolyl)indenyl) zirconium dichloride,
dimethylsilanediylbis(2-trimethylsilyl-4-(8-quinolyl) indenyl)zirconium dichloride,
methylphenylsilanediylbis(2-methyl-4-(8-quinolyl) indenyl)zirconium dichloride,
diphenylsilanediylbis(2-methyl-4-(8-quinolyl)indenyl) zirconium dichloride,
1,2-ethanediylbis(2-methyl-4-(8-quinolyl)indenyl) zirconium dichloride,
dimethylsilanediylbis(2-methyl-4,5-(2-azabenzo) indenyl)zirconium dichloride,
dimethylsilanediylbis(2-ethyl-4,5-(2-azabenzo)indenyl) zirconium dichloride,
dimethylsilanediylbis(2-n-butyl-4,5-(2-azabenzo) indenyl)zirconium dichloride,
dimethylsilanediylbis(2-i-propyl-4,5-(2-azabenzo) indenyl)zirconium dichloride,
dimethylsilanediylbis(2-phenyl-4,5-(2-azabenzo)indenyl) zirconium dichloride,
dimethylsilanediylbis(2-trimethylsilyl-4,5-(2-azabenzo) indenyl)zirconium dichloride,
methylphenylsilanediylbis(2-methyl-4, 5-(2-azabenzo) indenyl)zirconium dichloride,
diphenylsilanediylbis(2-methyl-4,5-(2-azabenzo)indenyl) zirconium dichloride,
1,2-ethanediylbis(2-methyl-4,5-(2-azabenzo)indenyl) zirconium dichloride,
dimethylsilanediylbis(2-methyl-4-(4-pyridyl)indenyl) zirconium dichloride,
dimethylsilanediylbis(2-ethyl-4,5-(4-pyridyl)indenyl) zirconium dichloride,
dimethylsilanediylbis(2-n-butyl-4,5-(4-pyridyl)indenyl) zirconium dichloride,
dimethylsilanediylbis(2-i-propyl-4,5-(4-pyridyl)indenyl) zirconium dichloride,
dimethylsilanediylbis(2-phenyl-4,5-(4-pyridyl)indenyl) zirconium dichloride,
dimethylsilanediylbis(2-trimethylsilyl-4, 5-(4-pyridyl) indenyl)zirconium dichloride,
methylphenylsilanediylbis(2-methyl-4, 5-(4-pyridyl) indenyl)zirconium dichloride,
diphenylsilanediylbis(2-methyl-4,5-(4-pyridyl)indenyl) zirconium dichloride,
1,2-ethanediylbis(2-methyl-4,5-(4-pyridyl)indenyl) zirconium dichloride,
dimethylsilanediylbis(2-methyl-4-(5-pyrimidyl)indenyl) zirconium dichloride,
dimethylsilanediylbis(2-ethyl-4,5-(5-pyrimidyl)indenyl) zirconium dichloride,
dimethylsilanediylbis(2-n-butyl-4,5-(5-pyrimidyl) indenyl)zirconium dichloride,
dimethylsilanediylbis(2-i-propyl-4,5-(5-pyrimidyl) indenyl)zirconium dichloride,
dimethylsilanediylbis(2-phenyl-4,5-(5-pyrimidyl) indenyl)zirconium dichloride,
dimethylsilanediylbis(2-trimethylsilyl-4,5-(5-pyrimidyl) indenyl)zirconium dichloride,
methylphenylsilanediylbis(2-methyl-4,5-(5-pyrimidyl) indenyl)zirconium dichloride,
diphenylsilanediylbis(2-methyl-4,5-(5-pyrimidyl) indenyl)zirconium dichloride,
1,2-ethanediylbis(2-methyl-4,5-(5-pyrimidyl)indenyl) zirconium dichloride,
dimethylsilanediylbis(2-methyl-4-(2-furanyl)indenyl) zirconium dichloride,
dimethylsilanediylbis(2-ethyl-4,5-(2-furanyl)indenyl) zirconium dichloride,
dimethylsilanediylbis(2-n-butyl-4,5-(2-furanyl)indenyl) zirconium dichloride,
dimethylsilanediylbis(2-i-propyl-4,5-(2-furanyl)indenyl) zirconium dichloride,
dimethylsilanediylbis(2-phenyl-4,5-(2-furanyl)indenyl) zirconium dichloride,
dimethylsilanediylbis(2-trimethylsilyl-4,5-(2-furanyl) indenyl)zirconium dichloride,
methylphenylsilanediylbis(2-methyl-4,5-(2-furanyl) indenyl)zirconium dichloride,
diphenylsilanediylbis(2-methyl-4,5-(2-furanyl)indenyl) zirconium dichloride,
1,2-ethanediylbis(2-methyl-4,5-(2-furanyl)indenyl) zirconium dichloride,
dimethylsilanediylbis(2-methyl-4-(2-fufuryl)indenyl) zirconium dichloride,
dimethylsilanediyl(2-methyl-4,5-(2-fufuryl)indenyl) (2-methyl-4-(2-pyridyl)indenyl)zirconium dichloride,
dimethylsilanediylbis(2-n-butyl-4,5-(2-fufuryl)indenyl) zirconium dichloride,
dimethylsilanediylbis(2-i-propyl-4,5-(2-fufuryl)indenyl) zirconium dichloride,
dimethylsilanediylbis(2-phenyl-4,5-(2-fufuryl)indenyl) zirconium dichloride,
dimethylsilanediylbis(2-trimethylsilyl-4,5-(2-fufuryl) indenyl)zirconium dichloride,
methylphenylsilanediylbis(2-methyl-4,5-(2-fufuryl) indenyl)zirconium dichloride,
diphenylsilanediylbis(2-methyl-4,5-(2-fufuryl)indenyl) zirconium dichloride, 1,2-ethanediyl(2-methyl-4,5-(2-fufuryl)indenyl)(2-methyl-4-(2-furanyl)indenyl)zirconium dichloride,
bis(2-methyl-4-(2-pyridyl)indenyl)zirconium dichloride,
dimethylsilanediylbis(4-(2-pyridyl)indenyl)zirconium dichloride,
(2-i-propyl-4-(2-pyridyl)indenyl)zirconium dichloride,
(2-phenyl-4-(2-pyridyl)indenyl)zirconium dichloride,
(2-trimethylsilyl-4-(2-pyridyl)indenyl)zirconium dichloride,
methylphenylsilanediylbis(4-(2-pyridyl)indenyl)zirconium dichloride,
diphenylsilanediylbis(4-(2-pyridyl)indenyl)zirconium dichloride,
1,2-ethanediylbis(4-(2-pyridyl)indenyl)zirconium dichloride,
bis(2-methyl-4-(2-pyridyl)-7-methylindenyl)zirconium dichloride,
dimethylsilanediylbis(4-(2-pyridyl)-7-methylindenyl)zirconium dichloride,
(2-i-propyl-4-(2-pyridyl)-7-methylindenyl)zirconium dichloride,
(2-phenyl-4-(2-pyridyl)-7-methylindenyl)zirconium dichloride,
(2-trimethylsilyl-4-(2-pyridyl)-7-methylindenyl)zirconium dichloride,
methylphenylsilanediylbis(4-(2-pyridyl)-7-methylindenyl)zirconium dichloride,
diphenylsilanediylbis(4-(2-pyridyl)-7-methylindenyl)zirconium dichloride,
1,2-ethanediylbis(4-(2-pyridyl)-7-methylindenyl)zirconium dichloride,
dimethylsilanediylbis(2-methyl-4-(2-pyridyl)-6-i-propylindenyl)hafnium dichloride,
dimethylsilanediylbis(4-(2-pyridyl)-6-i-propylindenyl)hafnium dichloride,
dimethylsilanediylbis(2-n-butyl-4-(2-pyridyl)-6-i-propylindenyl)hafnium dichloride,
bis(2-i-propyl-4-(2-pyridyl)-6-i-propylindenyl)hafnium dichloride,
dimethylsilanediylbis(2-phenyl-4-(2-pyridyl)-6-i-propylindenyl)hafnium dichloride,
dimethylsilanediylbis(2-trimethylsilyl-4-(2-pyridyl)-6-i-propylindenyl)hafnium dichloride,
methylphenylsilanediylbis(2-methyl-4-(2-pyridyl)-6-i-propylindenyl)hafnium dichloride,
diphenylsilanediylbis(2-methyl-4-(2-pyridyl)-6-i-propylindenyl)hafnium dichloride,
1,2-ethanediylbis(2-methyl-4-(2-pyridyl)-6-i-propylindenyl)hafnium dichloride,
dimethylsilanediyl(indenyl)(2-methyl-4-(3-quinolyl)indenyl)zirconium dichloride,
dimethylsilanediyl(indenyl)(2-ethyl-4-(3-quinolyl)indenyl)zirconium dichloride,
dimethylsilanediyl(indenyl)(2-n-butyl-4-(3-quinolyl)indenyl)zirconium dichloride,
dimethylsilanediyl(indenyl)(2-i-propyl-4-(3-quinolyl)indenyl)zirconium dichloride,
dimethylsilanediyl(indenyl)(2-phenyl-4-(3-quinolyl)indenyl)zirconium dichloride,
dimethylsilanediyl(indenyl)(2-trimethylsilyl-4-(3-quinolyl)indenyl)zirconium dichloride,
methylphenylsilanediyl(indenyl) (2-methyl-4-(3-quinolyl)indenyl)zirconium dichloride,
diphenylsilanediyl(indenyl)(2-methyl-4-(3-quinolyl)indenyl)zirconium dichloride,
1,2-ethanediyl(indenyl)(2-methyl-4-(3-quinolyl)indenyl)zirconium dichloride,
dimethylsilanediyl(2-methylindenyl)(2-methyl-4-(8-quinolyl)indenyl)zirconium dichloride,
dimethylsilanediyl(2-methylindenyl) (2-ethyl-4-(8-quinolyl)indenyl)zirconium dichloride,
dimethylsilanediyl(2-methylindenyl) (2-n-butyl-4-(8-quinolyl)indenyl)zirconium dichloride,
dimethylsilanediyl(2-methylindenyl) (2-i-propyl-4-(8-quinolyl)indenyl)zirconium dichloride,
dimethylsilanediyl(2-methylindenyl) (2-phenyl- 4-(8-quinolyl)indenyl)zirconium dichloride,
dimethylsilanediyl(2-methylindenyl)(2-trimethylsilyl-4-(8-quinolyl)indenyl)zirconium dichloride,
methylphenylsilanediyl(2-methylindenyl)(2-methyl-4-(8-quinolyl)indenyl)zirconium dichloride,
diphenylsilanediyl(2-methylindenyl)(2-methyl-4-(8-quinolyl)indenyl)zirconium dichloride,
1,2-ethanediyl(2-methylindenyl)(2-methyl-4-(8-quinolyl)indenyl)zirconium dichloride,
bis(2-methyl-4,5-(2-azabenzo)indenyl)zirconium dichloride,
dimethylsilanediylbis(4,5-(2-azabenzo)indenyl)zirconium dichloride,
dimethylsilanediylbis(2-n-butyl-4,5-(2-azabenzo)indenyl)hafnium dichloride,
bis(2-i-propyl-4,5-(2-azabenzo)indenyl)zirconium dichloride,
bis(2-phenyl-4,5-(2-azabenzo)indenyl)zirconium dichloride,
bis(2-trimethylsilyl-4,5-(2-azabenzo)indenyl)zirconium dichloride,
methylphenylsilanediylbis(4,5-(2-azabenzo)indenyl)zirconium dichloride,
diphenylsilanediylbis(4,5-(2-azabenzo)indenyl)zirconium dichloride,
1,2-ethanediylbis(4,5-(2-azabenzo)indenyl)zirconium dichloride,
dimethylsilanediyl(2-methyl-4-phenylindenyl)(2-methyl-4-(4-pyridyl)indenyl)zirconium dichloride,
dimethylsilanediyl(2-methyl-4-phenylindenyl)(2-ethyl-4,5-(4-pyridyl)indenyl)zirconium dichloride,
dimethylsilanediyl(2-methyl-4-phenylindenyl)(2-n-butyl-4,5-(4-pyridyl)indenyl)zirconium dichloride,
dimethylsilanediyl(2-methyl-4-phenylindenyl)(2-i-propyl-4,5-(4-pyridyl)indenyl)zirconium dichloride,
dimethylsilanediyl(2-methyl-4-phenylindenyl)(2-phenyl-4,5-(4-pyridyl)indenyl)zirconium dichloride,
dimethylsilanediyl(2-methyl-4-phenylindenyl)(2-trimethylsilyl-4,5-(4-pyridyl)indenyl)zirconium dichloride,
methylphenylsilanediyl(2-methyl-4-phenylindenyl)(2-methyl-4,5-(4-pyridyl)indenyl)zirconium dichloride,
diphenylsilanediyl(2-methyl-4-phenylindenyl)(2-methyl-4,5-(4-pyridyl)indenyl)zirconium dichloride,
1,2-ethanediyl(2-methyl-4-phenylindenyl)(2-methyl-4,5-(4-pyridyl)indenyl)zirconium dichloride,
dimethylsilanediyl(cyclopentadienyl)(2-methyl-4-(5-pyrimidyl)indenyl)zirconium dichloride, dimethylsilanediyl(cyclopentadienyl)(2-ethyl-4,5-(5-pyrimidyl)indenyl)zirconium dichloride,
dimethylsilanediyl(cyclopentadienyl)(2-n-butyl-4,5-(5-pyrimidyl)indenyl)zirconium dichloride,
dimethylsilanediyl(cyclopentadienyl)(2-i-propyl- 4,5-(5-pyrimidyl)indenyl)zirconium dichloride,
dimethylsilanediyl(cyclopentadienyl) (2-phenyl-4,5-(5-pyrimidyl)indenyl)zirconium dichloride,
dimethylsilanediyl(cyclopentadienyl)(2-trimethylsilyl-4,5-(5-pyrimidyl)indenyl)zirconium dichloride,
methylphenylsilanediyl(cyclopentadienyl)(2-methyl-4,5-(5-pyrimidyl)indenyl)zirconium dichloride,
diphenylsilanediyl(cyclopentadienyl)(2-methyl-4,5-(5-pyrimidyl)indenyl)zirconium dichloride,
1,2-ethanediyl(cyclopentadienyl)(2-methyl-4,5-(5-pyrimidyl)indenyl)zirconium dichloride,
dimethylsilanediyl(2-methyl-4,5-benzoindenyl)(2-methyl-4-(2-furanyl)indenyl)zirconium dichloride,
dimethylsilanediyl(2-methyl-4,5-benzoindenyl)(2-ethyl-4,5-(2-furanyl)indenyl)zirconium dichloride,
dimethylsilanediyl(2-methyl-4,5-benzoindenyl)(2-n-butyl-4,5-(2-furanyl)indenyl)zirconium dichloride,
dimethylsilanediyl(2-methyl-4,5-benzoindenyl)(2-i-propyl-4,5-(2-furanyl)indenyl)zirconium dichloride,
dimethylsilanediyl(2-methyl-4,5-benzoindenyl)(2-phenyl-4,5-(2-furanyl)indenyl)zirconium dichloride,
dimethylsilanediyl(2-methyl-4,5-benzoindenyl)(2-trimethylsilyl-4,5-(2-furanyl)indenyl)zirconium dichloride,
methylphenylsilanediyl(2-methyl-4,5-benzoindenyl)(2-methyl- 4,5-(2-furanyl)indenyl)zirconium dichloride,
diphenylsilanediyl(2-methyl-4,5-benzoindenyl)(2-methyl-4,5-(2-furanyl)indenyl)zirconium dichloride,
1,2-ethanediyl(2-methyl-4,5-benzoindenyl)(2-methyl-4,5-(2-furanyl)indenyl)zirconium dichloride,
dimethylsilanediyl(2-methyl-4-phenylindenyl)(2-methyl-4-(2-fufuryl)indenyl)zirconium dichloride,
dimethylsilanediyl(2-methyl-4-phenylindenyl)(2-ethyl-4,5-(2-fufuryl)indenyl)zirconium dichloride,
dimethylsilanediyl(2-methyl-4-phenylindenyl)(2-n-butyl-4,5-(2-fufuryl)indenyl)zirconium dichloride,
dimethylsilanediyl(2-methyl-4-phenylindenyl)(2-i-propyl-4,5-(2-fufuryl)indenyl)zirconium dichloride,
dimethylsilanediyl(2-methyl-4-phenylindenyl) (2-phenyl-4,5-(2-fufuryl)indenyl)zirconium dichloride,
dimethylsilanediyl(2-methyl-4-phenylindenyl)(2-trimethylsilyl-4,5-(2-fufuryl)indenyl)zirconium dichloride,
methylphenylsilanediyl(2-methyl-4-phenylindenyl)(2-methyl-4,5-fufuryl)indenyl)zirconium dichloride,
diphenylsilanediyl(2-methyl-4-phenylindenyl)(2-methyl-4,5-(2-fufuryl)indenyl)zirconium dichloride,
1,2-ethanediyl(2-methyl-4-phenylindenyl)(2-methyl-4,5-(2-fufuryl)indenyl)zirconium dichloride,
dimethylsilanediyl(methylcyclopentadienyl)(2-methyl-4,6-bis(2-pyridyl)indenyl)zirconium dichloride,
dimethylsilanediyl(methylcyclopentadienyl)(2-ethyl-4,6-bis(2-pyridyl)indenyl)zirconium dichloride,
dimethylsilanediyl(methylcyclopentadienyl)(2-n-butyl-4,6-bis(2-pyridyl)indenyl)zirconium dichloride,
dimethylsilanediyl(methylcyclopentadienyl)(2-i-propyl-4,6-bis(2-pyridyl)indenyl)zirconium dichloride,
dimethylsilanediyl(methylcyclopentadienyl)(2-phenyl-4,6-bis(2-pyridyl)indenyl)zirconium dichloride,
dimethylsilanediyl(methylcyclopentadienyl)(2-trimethylsilyl-4,6-bis(2-pyridyl)indenyl)zirconium dichloride,
methylphenylsilanediyl(methylcyclopentadienyl)(2-methyl-4,6-bis(2-pyridyl)indenyl)zirconium dichloride,
diphenylsilanediyl(methylcyclopentadienyl)(2-methyl-4,6-bis(2-pyridyl)indenyl)zirconium dichloride,
1,2-ethanediyl(methylcyclopentadienyl)(2-methyl-4,6-bis(2-pyridyl)indenyl)zirconium dichloride,
dimethylsilanediyl(fluorenyl)(2-methyl-4-(3-quinolyl)indenyl)zirconium dichloride,
dimethylsilanediyl(fluorenyl)(2-ethyl-4-(3-quinolyl)indenyl)zirconium dichloride,
dimethylsilanediyl(fluorenyl)(2-n-butyl-4-(3-quinolyl)indenyl)zirconium dichloride,
dimethylsilanediyl(fluorenyl)(2-i-propyl-4-(3-quinolyl)indenyl)zirconium dichloride,
dimethylsilanediyl(fluorenyl)(2-phenyl-4-(3-quinolyl)indenyl)zirconium dichloride,
dimethylsilanediyl(fluorenyl)(2-trimethylsilyl-4-(3-quinolyl)indenyl)zirconium dichloride,
methylphenylsilanediyl(fluorenyl)(2-methyl-4-(3-quinolyl)indenyl)zirconium dichloride,
diphenylsilanediyl(fluorenyl)(2-methyl-4-(3-quinolyl)indenyl)zirconium dichloride,
1,2-ethanediyl(fluorenyl)(2-methyl-4-(3-quinolyl)indenyl)zirconium dichloride,
dimethylsilanediylbis(2-methyl-6-(8-quinolyl)indenyl)zirconium dichloride,
dimethylsilanediylbis(2-ethyl-6-(8-quinolyl)indenyl)zirconium dichloride,
dimethylsilanediylbis(2-n-butyl-6-(8-quinolyl)indenyl)zirconium dichloride,
dimethylsilanediylbis(2-i-propyl-6-(8-quinolyl)indenyl)zirconium dichloride,
dimethylsilanediylbis(2-phenyl-6-(8-quinolyl)indenyl)zirconium dichloride,
dimethylsilanediylbis(2-trimethylsilyl-6-(8-quinolyl)indenyl)zirconium dichloride,
methylphenylsilanediylbis(2-methyl-6-(8-quinolyl)indenyl)zirconium dichloride,
diphenylsilanediylbis(2-methyl-6-(8-quinolyl)indenyl)zirconium dichloride,
1,2-ethanediylbis(2-methyl-6-(8-quinolyl)indenyl)zirconium dichloride,
dimethylsilanediyl(methylcyclopentadienyl)(2-methyl-4,5-(2-azabenzo)indenyl)zirconium dichloride,
dimethylsilanediyl(methylcyclopentadienyl)(2-ethyl-4,5-(2-azabenzo)indenyl)zirconium dichloride,
dimethylsilanediyl(methylcyclopentadienyl)(2-n-butyl-4,5-(2-azabenzo)indenyl)zirconium dichloride,
dimethylsilanediyl(methylcyclopentadienyl)(2-i-propyl-4,5-(2-azabenzo)indenyl)zirconium dichloride,
dimethylsilanediyl(methylcyclopentadienyl)(2-phenyl-4,5-(2-azabenzo)indenyl)zirconium dichloride,
dimethylsilanediyl(methylcyclopentadienyl)(2-trimethylsilyl-4,5-(2-azabenzo)indenyl)zirconium dichloride,
methylphenylsilanediyl(methylcyclopentadienyl)(2-methyl-4,5-(2-azabenzo)indenyl)zirconium dichloride, diphenylsilanediyl(methylcyclopentadienyl)(2-methyl-4,5-(2-azabenzo)indenyl)zirconium dichloride, 1,2-ethanediyl(methylcyclopentadienyl)(2-methyl-4,5-(2-azabenzo)indenyl)zirconium dichloride, dimethylsilanediylbis( (4-pyridyl)cyclopentadienyl) zirconium dichloride, dimethylsilanediylbis(ethyl-(4-pyridyl)cyclopentadienyl) zirconium dichloride, dimethylsilanediylbis(n-butyl-(4-pyridyl) cyclopentadienyl)zirconium dichloride, dimethylsilanediylbis(i-propyl-(4-pyridyl) cyclopentadienyl)zirconium dichloride, dimethylsilanediylbis(phenyl-(4-pyridyl) cyclopentadienyl)zirconium dichloride, dimethylsilanediylbis(trimethylsilyl-(4-pyridyl) cyclopentadienyl)zirconium dichloride, methylphenylsilanediylbis(methyl-(4-pyridyl) cyclopentadienyl)zirconium dichloride, diphenylsilanediylbis((4-pyridyl)cyclopentadienyl) zirconium dichloride, 1,2-ethanediylbis((4-pyridyl)cyclopentadienyl)zirconium dichloride, dimethylsilanediyl(cyclopentadienyl)(4-(5-pyrimidyl) cyclopentadienyl)zirconium dichloride, (cyclopentadienyl)((5-pyrimidyl)cyclopentadienyl) zirconium dichloride and dimethylsilanediyl (methylcyclopentadienyl)(n-butyl-(5-pyrimidyl)cyclopentadienyl)zirconium dichloride.

10. A metallocene compound of the formula I

$$R^5{}_nCp^1Cp^2M^1R^1R^2 \quad\quad (I)$$

where

Cp$^1$ and Cp$^2$ are, independently of one another, identical or different and are each an unsubstituted or substituted cyclopentadienyl group, n=zero, R$^5$ is a bridge, M$^1$ is a metal of group IVb, Vb or VIb of the Periodic Table of the Elements, R$^1$ and R$^2$ are identical or different and are each a hydrogen atom, a C$_1$–C$_{40}$-hydrocarbon group, —OH group, halogen atom or —NR$^6{}_2$ group where R$^6$ are identical or different and are each a C$_1$–C$_{10}$-alkyl group or a C$_6$–C$_{14}$-aryl group wherein at least one of the two groups Cp$^1$ and Cp$^2$ is a substituted cyclopentadienyl group which bears at least one cyclic C$_3$–C$_{20}$-containing at least one heteroatom in the ring, wherein said heteroatom is selected from the group consisting of O, N, P, Si and S or which bears a fused-on C$_2$–C$_{20}$-ring.

11. A metallocene compound of the formula I

$$R^5{}_nCp^1Cp^2M^1R^1R^2 \quad\quad (I)$$

where

Cp$^1$ and Cp$^2$ are, independently of one another, identical or different and are each an unsubstituted or substituted cyclopentadienyl group, n=zero or 1, R$^5$ is a bridge, M$^1$ is a metal of group IVb, Vb or VIb of the Periodic Table of the Elements, R$^1$ and R$^2$ are identical or different and are each a hydrogen atom, a C$_1$–C$_{40}$-hydrocarbon group, —OH group, halogen atom or —NR$^6{}_2$ group where R$^6$ are identical or different and are each a C$_1$–C$_{10}$-alkyl group or a C$_6$–C$_{14}$-aryl group wherein at least one of the two groups Cp$^1$ and Cp$^2$ is a substituted cyclopentadienyl group which bears a fused on C$_2$–C$_{20}$-ring system containing at least one heteroatom in the ring wherein said heteroatom is selected from the group consisting of O, N, P, Si and S.

12. A metallocene compound of the formula I

$$R^5{}_nCp^1Cp^2M^1R^1R^2 \quad\quad (I)$$

where

Cp$^1$ and Cp$^2$ are, independently of one another, identical or different and are each an unsubstituted or substituted cyclopentadienyl group, n=zero or 1, R$^5$ is a bridge, M$^1$ is a metal of group IVb, Vb or VIb of the Periodic Table of the Elements, R$^1$ and R$^2$ are identical or different and are each a hydrogen atom, a C$_1$–C$_{40}$-hydrocarbon group, —OH group, halogen atom or —NR$^6{}_2$ group where R$^6$ are identical or different and are each a C$_1$–C$_{10}$-alkyl group or a C$_6$–C$_{14}$-aryl group wherein at least one of the two groups Cp$^1$ and Cp$^2$ is a substituted cyclopentadienyl group which bears at least one cyclic C$_3$–C$_{30}$-group containing at least one heteroatom in the ring, or which bears a fused-on C$_2$–C$_{30}$-ring wherein said at least one heteroatom is O, S or Si.

13. A metallocene compound of the formula I

$$R^5{}_nCp^1Cp^2M^1R^1R^2 \quad\quad (I)$$

where

Cp$^1$ and Cp$^2$ are, independently of one another, identical or different and are each an unsubstituted or substituted cyclopentadienyl group, n=zero or 1, R$^5$ is a bridge, M$^1$ is a metal of group IVb, Vb or VIb of the Periodic Table of the Elements, R$^1$ and R$^2$ are identical or different and are each a hydrogen atom, a C$_1$–C$_{40}$-hydrocarbon group, —OH group, halogen atom or —NR$^6{}_2$ group where R$^6$ are identical or different and are each a C$_1$–C$_{10}$-alkyl group or a C$_6$–C$_{14}$-aryl group wherein at least one of the two groups Cp$^1$ and Cp$^2$ is a substituted cyclopentadienyl group which bears at least one cyclic C$_3$–C$_{20}$-containing at least one heteroatom in the ring, or which bears a fused-on C$_2$–C$_{20}$-ring wherein the substituted cyclopentadienyl group does not contain the heteroatom on the five membered cyclopentadienyl ring wherein said heteroatom is selected from the group consisting of O, N, P, Si and S.

\* \* \* \* \*